(12) United States Patent
Bidault et al.

(10) Patent No.: US 9,512,279 B2
(45) Date of Patent: Dec. 6, 2016

(54) INTERPENETRATING POLYMER NETWORK

(71) Applicant: Universite Cergy-Pontoise, Cergy (FR)

(72) Inventors: Laurent Bidault, Vaux-sur-Seine (FR);
Odile Fichet, Poissy (FR); Veronique Larreta Garde, L'isle Adam (FR);
Cedric Vancaeyzeele, Vernouillet (FR);
Mathilde Hindie, Saint Ouen l'Aumone (FR); Marie Deneufchatel, Jouy-le-Moutier (FR)

(73) Assignee: Universite Cegy-Pontoise, Cergy (FR)

( * ) Notice: Subject to any disclaimer, the term of this patent is extended or adjusted under 35 U.S.C. 154(b) by 133 days.

(21) Appl. No.: 14/132,410

(22) Filed: Dec. 18, 2013

(65) Prior Publication Data
US 2015/0166735 A1 Jun. 18, 2015

(51) Int. Cl.

| | |
|---|---|
| *C08J 3/075* | (2006.01) |
| *C08J 3/24* | (2006.01) |
| *C08L 89/00* | (2006.01) |
| *C08L 51/00* | (2006.01) |
| *A61L 15/32* | (2006.01) |
| *A61L 15/24* | (2006.01) |
| *A61L 15/64* | (2006.01) |
| *A61L 15/40* | (2006.01) |
| *A61L 27/16* | (2006.01) |
| *A61L 27/22* | (2006.01) |
| *A61L 27/34* | (2006.01) |
| *A61L 27/36* | (2006.01) |
| *A61L 27/54* | (2006.01) |
| *A61L 29/04* | (2006.01) |
| *A61L 29/08* | (2006.01) |
| *A61L 29/16* | (2006.01) |
| *A61L 31/04* | (2006.01) |
| *A61L 31/10* | (2006.01) |
| *A61L 31/16* | (2006.01) |
| *A61L 26/00* | (2006.01) |
| *C08G 18/62* | (2006.01) |
| *C08G 18/81* | (2006.01) |
| *C08H 1/00* | (2006.01) |

(52) U.S. Cl.
CPC ............ *C08J 3/075* (2013.01); *A61L 15/24* (2013.01); *A61L 15/32* (2013.01); *A61L 15/40* (2013.01); *A61L 15/64* (2013.01); *A61L 26/0014* (2013.01); *A61L 26/0042* (2013.01); *A61L 26/0052* (2013.01); *A61L 27/16* (2013.01); *A61L 27/225* (2013.01); *A61L 27/34* (2013.01); *A61L 27/3633* (2013.01); *A61L 27/54* (2013.01); *A61L 29/041* (2013.01); *A61L 29/047* (2013.01); *A61L 29/049* (2013.01); *A61L 29/085* (2013.01); *A61L 29/16* (2013.01); *A61L 31/046* (2013.01); *A61L 31/048* (2013.01); *A61L 31/10* (2013.01); *A61L 31/16* (2013.01); *C08G 18/6212* (2013.01); *C08G 18/8116* (2013.01); *C08H 1/00* (2013.01); *C08J 3/246* (2013.01); *C08L 51/00* (2013.01); *C08L 89/00* (2013.01); *A61L 2400/04* (2013.01); *A61L 2430/34* (2013.01); *C08J 2329/04* (2013.01); *C08J 2351/00* (2013.01); *C08J 2389/00* (2013.01); *C08L 2201/06* (2013.01); *C08L 2203/02* (2013.01); *C08L 2205/04* (2013.01); *C08L 2312/06* (2013.01)

(58) Field of Classification Search
None
See application file for complete search history.

(56) References Cited

U.S. PATENT DOCUMENTS

| | | | | |
|---|---|---|---|---|
| 4,423,099 A | * | 12/1983 | Mueller | ............... A01N 25/10 424/419 |
| 5,644,049 A | * | 7/1997 | Giusti | .................. A61L 27/26 523/113 |
| 5,733,563 A | * | 3/1998 | Fortier | ................. A61L 15/32 424/422 |
| 6,224,893 B1 | * | 5/2001 | Langer | ................ A61K 9/0019 424/423 |
| 2005/0187146 A1 | * | 8/2005 | Helmus | ................. A61L 27/22 424/85.2 |
| 2006/0134050 A1 | * | 6/2006 | Griffith | .................. A61F 2/10 424/70.16 |
| 2008/0317818 A1 | * | 12/2008 | Griffith | ............... A61K 9/0051 424/427 |

(Continued)

FOREIGN PATENT DOCUMENTS

| | | | | |
|---|---|---|---|---|
| FR | 2938544 A1 | * | 5/2010 | ......... A61L 24/0031 |
| WO | 2010058132 | | 5/2010 | |

OTHER PUBLICATIONS

Bidault, Laurent, et al. "Self-Supported Fibrin-Polyvinyl Alcohol Interpenetrating Polymer Networks: An Easily Handled and Rehydratable Biomaterial." Biomacromolecules 14.11 (2013): 3870-3879.*

(Continued)

Primary Examiner — Bethany Barham
Assistant Examiner — Peter Anthopolos
(74) Attorney, Agent, or Firm — Banner & Witcoff, Ltd.

(57) ABSTRACT

The present invention relates to a material as interpenetrating polymer network (IPN) associating a gel with a co-network of functionalized synthetic polymer and functionalized protein as well as a method of the manufacture of such a material. In particular, the invention relates to a material as interpenetrating polymer network associating a fibrin gel with a co-network of polyvinylalcohol and albumin thank to methacrylate bridges, with improved biodegradability properties.

19 Claims, 7 Drawing Sheets

(56) References Cited

U.S. PATENT DOCUMENTS

| | | | | |
|---|---|---|---|---|
| 2012/0225040 A1* | 9/2012 | Hossainy | ............ | A61K 9/0024 424/93.7 |
| 2012/0265165 A1* | 10/2012 | Bucknall | ................ | A61L 27/26 604/500 |
| 2012/0288564 A1* | 11/2012 | Kurisawa | ............ | C12N 5/0068 424/484 |

OTHER PUBLICATIONS

Gonen-Wadmany, Maya, Liat Oss-Ronen, and Dror Seliktar. "Protein-polymer conjugates for forming photopolymerizable biomimetic hydrogels for tissue engineering." Biomaterials 28.26 (2007): 3876-3886.*

Hoshikawa, Atsuto, et al. "Encapsulation of chondrocytes in photopolymerizable styrenated gelatin for cartilage tissue engineering." Tissue engineering 12.8 (2006): 2333-2341.*

Martens, P., and K. S. Anseth. "Characterization of hydrogels formed from acrylate modified poly (vinyl alcohol) macromers." Polymer 41.21 (2000): 7715-7722.*

Nguyen, Kytai Truong, and Jennifer L. West. "Photopolymerizable hydrogels for tissue engineering applications." Biomaterials 23.22 (2002): 4307-4314.*

Schmedlen, Rachael H., Kristyn S. Masters, and Jennifer L. West. "Photocrosslinkable polyvinyl alcohol hydrogels that can be modified with cell adhesion peptides for use in tissue engineering." Biomaterials 23.22 (2002): 4325-4332.*

Ifkovits, Jamie L., and Jason A. Burdick. "Review: Photopolymerizable and degradable biomaterials for tissue engineering applications." Tissue engineering 13.10 (2007): 2369-2385.*

Akpalo et al., Fibrin-polyethylene oxide interpenetrating polymer networks: "New self-supported biomaterials combining the properties of both protein gel and synthetic polymer", Acta Biomaterialia, vol. 7, pp. 2418-2427, dated 2011.

Kundu, et al., "Silk fibroin/poly(vinyl alcohol) photocrosslinked hydrogels for delivery of macromolecular drugs", Acta Biomaterialia, vol. 8, pp. 1720-1729, dated 2012.

* cited by examiner

INTERPENETRATING POLYMER NETWORK

The present invention relates to a material as interpenetrating polymer network (IPN) associating a gel with a co-network of synthetic polymer and protein as well as a method of the manufacture of such a material. In particular, the invention relates to a material as interpenetrating polymer network associating a fibrin gel with a co-network of polyvinylalcohol and albumin thank to methacrylate bridges, with improved biodegradability properties.

The invention also refers to use of this material in biomedical applications, such as drug delivery vehicle, encapsulation material, wound dressing, scaffold for tissue engineering, hemostatic dressing, surgical dressing, as a coating for medical devices such as stents, heart valves, catheters, vascular prosthetic filters etc. Such materials may also be used for eukaryotic cell culture, or as support for active molecules such as healing agents, growth factors, antibiotics, bactericidal, bacteriostatic or enzymes.

The definition of a gel corresponds to a nonfluid colloidal network or polymer network that is expanded throughout its whole volume by a fluid.

A gel can be made of:
(i) a covalent polymer network, e.g., a network formed by crosslinking polymer chains or by nonlinear polymerization. This type of gel is usually called "chemical gel". A chemical gel is a supramolecular assembly whose molecules are associated by high energy bonds (covalent bonds). The stability of this assembly is very large. These gels have improved chemical stability, the only way to degrade them is to destroy the covalent network bonding.
(ii) a polymer network formed through the physical aggregation or supramolecular assembly of polymer chains, caused by low energy bonds such as hydrogen bonds or Van der Waals bonds, crystallization, helix formation, complexation, that results in regions of local order acting as the network junction points. This type of gel is usually called "physical gel". The stability of this assembly is associated with a specific range of physico-chemical conditions (pH, concentration of molecules, temperature, solvent quality, ionic strength, etc). Outside this range, the mixture is liquid. Thus, a change in the parameters of the medium can lead to the destruction of the scaffold and induce a gel/sol transition. Some "physical" gels are well known such as ones obtained from macromolecules or polymers of natural origin like proteins or polysaccharides. Gelatin, alginate, pectin or starch may be mentioned as example of macromolecules capable of forming physical gels.

Obtaining a material in the form of a hydrogel is a real need especially in the medical field. Hydrogels are insoluble three-dimensional (3-D) networks of hydrophilic homopolymers, co-polymers or macromers with a swelling capacity in aqueous environments. The hydrogels have the property of being very elastic and rich in solvent. Their size and shape may vary according to environmental stimuli such as pH, temperature, solvent composition, ionic strength, electric and magnetic fields. Hydrogels obtained from biological origin, usually called biogels, are hydrophilic networks that hold large amounts of water without dissolving and thus have similar physical characteristics to those of biological soft tissue. Furthermore, hydrogels synthesized from natural macromers generally induce fewer immunogenic reactions as they are produced from basic molecules already used by the body. Synthetic derivative hydrogels have the advantage of controlling the gel properties, which can be tailored through the chemical nature of the synthetic precursors, their specific molecular weight and cross-linking densities for example. Biological molecules may be incorporated into synthetic hydrogel networks to improve cell attachment. Hydrogels have a high permeability to oxygen, nutrients and other water-soluble metabolites and are well adapted for growth of tissue structures. Hydrogels are attractive for drug delivery due to their good compatibility with hydrophilic and macromolecular compounds (proteins, polysaccharides, oligonucleotides), their biocompatibility and possibility to regulate the distribution of drugs through the control of their swelling, their crosslinking density or degradation for example. Hydrogels are interesting for a localized diffusion since they can be formed in situ and thus adhere to and comply with the target tissues. This use for local delivery of active ingredients appears to act synergistically with the barrier effect of the hydrogels. Hydrogels have also been investigated as potential materials for tissue regeneration or skin substitute which use constitute one very promising application.

Fibrin is made from fibrinogen, a 340 kDa glycoprotein of hepatic origin. Fibrinogen is an anionic polyelectrolyte under physiological conditions and therefore cannot join or aggregate. The hydrolysis of fibrinogen by thrombin, a serum protease, leads to the release of small peptide fragments and obtaining fibrin. Intermolecular interactions become possible, through low energy forces, thereby creating a physical network fibrin gel.

Fibrin gels physiologically form the basis of wound repair and haemostasis. Fibrin gels are used as surgical glue and are attractive as biocompatible and biodegradable materials. However, at physiological concentrations (4.8 mg mL$^{-1}$), fibrin hydrogels are soft, cannot be easily handled and do not self-stand.

Fibrin matrices with improved mechanical properties have been designed by increasing fibrinogen or thrombin concentrations. However, while more rigid materials are needed, the physiological-like organization of fibrin networks, which is perfectly adapted to the various cells implied in physiological processes such as wound healing, must be maintained. Another approach to improving self-supported fibrin gels may be used, consisting of the combination of hydrogel with a synthetic polymer. A material showing the strength and elasticity necessary to be easily handled would thus be obtained, while maintaining all the properties of a fibrin gel.

However, the macromolecule blend is generally thermodynamically unfavorable, and macroscopic phase separation generally occurs. Thus, an original pathway was developed to obtain an easily handled fibrin-based material: fibrin gel is associated with a synthetic polymer network inside interpenetrating polymer network (IPN) architecture. IPN are defined as a combination of two or more polymer networks, at least partially interlaced, synthesized in juxtaposition. The entanglement of two polymers, leads to forced miscibility, compared with usual blends.

WO2010/058132 discloses a material in the form of an interpenetrating network involving fibrin gel with a network of synthetic polymer (obtained by polymerization and cross-linking monomer such as a polyethylene oxide-functionalized vinyl, acrylate, methacrylate or allyl, optionally with a second monomer derivative such as a functionalized polyethylene glycol). While the mechanical properties of such a material appear good, their biodegradability and resorption in situ is limited and not adequate for all applications.

In Acta Biomaterialia 7 (2011) 2418-2427, are disclosed, materials made of a fibrin gel interpenetrated with polyethylene oxide dimethacrylate polymerized/crosslinked network. It is stated that the mechanical properties of the fibrin gel can thus be improved by the presence of the polyethylene oxide network. The teaching of this document is basically the same as WO2010/058132.

Kundu et al (Biomaterialia Acta 8 (2012) 1720-1729) disclose hydrogels comprising a network of PVA functionalized (via function methacrylate) and associated with a silk protein gel. In this document, the silk protein does not participate in the crosslinking of the PVA polymer and the biodegradability is also limited.

Fibrin has often been associated with type I collagen to improve the mechanical properties of collagen. Alginate has been also included in fibrin-based hydrogels. Fibrin-alginate IPN shows dynamic mechanical properties that can be employed to enhance tissue development relative to a single hydrogel. This association provides a dynamic mechanical environment, which facilitates the growth of organized cell clusters. However, the gels formed from organic molecules are soft materials and while biodegradable. Their main drawback is a poor mechanical resistance.

Furthermore, gels and materials of the prior art can hardly keep their properties after being dehydrated and rehydrated. There is thus a real need for a material that can be easily handled, which has the properties of a gel dimensionally stable, improved degradation ability, that can be stored dehydrated and can be fully rehydrated upon extemporaneous use. There is also a need for a material that can contain living cell embedded within it and can sustain the growth of those embedded cell and that can also be frozen while preserving the viability of the encapsulated cells.

As stated earlier, there is a need to have a material gel which would combine the properties of physical and chemical gels. Such a material would be stable and maintains its structural integrity and thus its properties throughout the duration of its handling and use, but would be degradable or labile within biological environment, i.e. can be destabilized and degraded when desired. To date, most of the easily handled gels lack lability and biodegradability within the biological environment, i.e. after implantation in the body. This is of particular importance in the cases of patients victims of wounds and burns in which cases it is important to ensure that the material creates the least possible reaction from the host. The present invention is specifically intended to meet this need by providing a method for preparing a material as interpenetrating polymer network (IPN) associating a gel with a co-network of functionalized synthetic polymer crosslinked with a functionalized protein, comprising the steps of:

i) preparing a first mixture by introducing into a buffer
   a. a gel forming solution or a gel forming precursor solution,
   b. a synthetic polymer selected in the group consisting of polyvinyl alcohol (PVA), polyglycolic acid (PGA), polylactic acid (PLA), polycaprolactone (PCL), poly(N-vinylpyrolidone), poly(2-hydroxy ethyl methacrylate) (PHEMA), polyethyleneoxide (PEO), and derivatives thereof, wherein the polymer is functionalized with grafted chemical groups X, X being selected in the group consisting of acrylate, methacrylate, vinyl, allyl and styrene derivatives,
   c. a protein functionalized with grafted chemical groups X, wherein X is has the same meaning than in b)
   d. a polymerization initiator,
ii) preparing a second reaction mixture by optionally adding a gelification activator of the formation of the gel to the first mixture prepared in i),
iii) incubating the reaction mixture obtained in i) or in ii) at a temperature and during a time sufficient to allow formation of the gel, and
iv) performing a polymerizing and crosslinking of the functionalized synthetic polymer with the functionalized protein.

The method of the invention allows preparing a material in the form of interpenetrating polymer network (IPN) which is homogeneous, self-supported, easy to handle, stable over time, dimensionally stable and biodegradable. Gelation on the one hand and polymerization and crosslinking on the other hand can take place simultaneously or sequentially.

In the remaining part of the description, the synthetic polymer which is functionalized with grafted chemical groups X, X being selected in the group consisting of acrylate, methacrylate, vinyl, allyl and styrene is called functionalized synthetic polymer.

Similarly, the protein which is functionalized with grafted chemical groups X, wherein X is selected in the group consisting of acrylate, methacrylate, vinyl, allyl and styrene is called functionalized protein.

In order to ensure the establishment of the co-network by covalent bonds between the polymer and the protein, the functionalized synthetic polymer and the functionalized protein each comprise at least two grafted chemical groups X. The functionalized protein thus comprises at least two grafted chemical group X, preferably at least three, more preferably at least 4, even more preferably at least five. The maximal number of grafted chemical groups X on the functionalized protein is not critical and is dependent on the number and accessibility of amino acid side chain available for grafting. The highest number of grafted chemical groups X, the highest the strength of the link between the protein and the synthetic polymer.

Similarly the functionalized synthetic polymer thus comprises at least two grafted chemical group X, preferably at least three chemical groups X, more preferably at least 4 chemical groups X, even more preferably at least five chemical group X. Because of the chain length of the synthetic polymer, the number of grafted chemical groups X can be up to 20, particularly up to 30, particularly up to 40, even more particularly up to 50 and even more particularly up to 60. The number of grafted chemical groups X will be dependent upon the molar weight of the polymer and the number of repeat units. Typically in the case of PVA, particularly PVA 16000, used as synthetic polymer, the number of grafted chemical groups X can be such as 1 group X is grafted for 5 to 100 repeat units, particularly 1 group X for 30 to 70 repeat units, more particularly 1 group X for about 50 repeat units. In the case of PVA 16000 the number of groups X, particularly methacrylate groups, is about 5 to 20, particularly 5 to 10, even more particularly around 7 groups per molecule.

In the context of the present invention, by "buffer" is meant an aqueous solution whose water content is at least 30% by weight, up to 99% by total weight of solvent and maintains approximately the same pH despite the addition of small amounts of an acid, a base or a dilution. The water content of the buffer is in particular 70 to 98% by total weight of the solvent.

Groups X grafted on the synthetic polymer and Groups X grafted on the protein may be the same or different provided that they can react to create a covalent bond crosslinking the protein and the synthetic polymer.

The buffer may further comprise other solvents selected from the group comprising methanol, ethanol, pyridine, acetone, acetic acid, DMSO, dichloromethane. The buffer may also comprise cosolvants such as glycerol, sorbitol, mannitol or any other polyol.

For example buffer includes phosphate buffers, Hepes, Tris, sodium barbital, Tris-maleate.

Throughout the duration of the process, the pH of the aqueous medium is maintained between 6 and 8 by means of a buffer solution, for example a trihydroxyaminomethane solution (Tris).

The gel can be a physical gel or a chemical gel. In a preferred embodiment it is a physical gel.

The gel forming solution or gel forming precursor solution can be a solution containing a gel forming polymer able to form a gel such as polysaccharide polymer or polypeptide polymer without or with the presence of a gelification activator. As a matter of example, such a gelification activator maybe thrombin and calcium when the gel forming precursor solution is fibrinogen containing solution and in that case the obtained gel is a physical gel, a fibrin gel.

In one embodiment of the present invention, the physical gel forming precursor solution is a fibrinogen containing solution. When a fibrinogen containing solution is used, the gelification activator of the formation of the physical gel is selected in the group consisting of thrombin and calcium, used alone or in combination. Indeed, in the case the gel forming precursor solution is fibrinogen, the activator is a combination of thrombin and calcium. If the fibrinogen solution already contains calcium, then the activator will be thrombin alone. In the case of the use of plasma as gel forming precursor solution, since plasma already contains thrombin, the activator will be calcium alone.

In an embodiment the physical gel forming precursor solution containing fibrinogen is serum which naturally contains fibrinogen.

In another embodiment, the physical gel forming precursor solution containing fibrinogen is plasma, which contains fibrinogen.

While plasma does contain thrombin and calcium, it may be useful to add additional calcium and/or thrombin in the reaction mixture in order to facilitate the formation of fibrin gel.

Besides being an autologous fluid which can be collected from the patient, plasma is also useful as a tank of healing biomolecules, including proteins (albumins and globulins), growth factors, and also fibrinogen which when placed in the presence of thrombin and its cofactor, calcium, may be cleaved to form a fibrin gel.

Plasma, as blood derivative, presents a real interest in the field of tissue engineering because of its bioavailability, because it contains growth factors, and molecules that are useful for wound healing, such as fibronectin which is a cell adhesion factor.

Plasma contains a number of proteins capable of forming a gel network (especially fibrinogen forming fibrin gel). In the context of the present invention, it is thus possible to isolate the plasma of a patient in need of care, for manufacturing a fully autologous material according to the present invention, such material would participate in wound healing without causing rejection or secondary effect.

The material manufactures with the use of blood products, such as plasma, present the advantage of mimicking the tissue microenvironment.

Materials based on human proteins stemming from plasma also have the enormous potential as matrix that can be colonized by cells and that is biodegradable in situ, ie within the body, as well as self-supported. A very promising property of the present material according to the present invention is that it can be of particular interest with patients suffering from wounds and burns. Indeed, the use of blood plasma from the patient himself ensures that the material causes the least possible reaction from the host. That promising solution according to the invention wherein the synthesis of the material according to the invention is achieved with the use of the blood plasma of the patient is particularly advantageous.

In the context of the present invention, the expression "gelification activator" relates to a compound which is able to and necessary for the formation of the gel. Such a gelification activator may be an enzyme and/or an ion for example.

In the case of fibrinogen or fibrinogen containing solution, the formation of fibrin as physical gel is triggered by the action of thrombin, a serum protease, and calcium, which leads to the release of small peptide fragments allowing creation of intermolecular interactions through low energy forces, thereby creating a physical network fibrin.

Fibrinogen may be for example human fibrinogen, pig fibrinogen or beef fibrinogen. In a particular embodiment the fibrinogen is human fibrinogen, obtained from human serum or from human plasma.

In another embodiment, the physical gel forming precursor solution may be a polysaccharide such as alginate or pectine and the gelification activator is calcium.

In a further embodiment, the gel precursor solution may also be a gelatin solution and the gelification activator is a crosslinking agent such as glutaraldehyde or the enzyme transglutaminase which allows the formation of gelatin gel, which in this case is a chemical gel.

In an embodiment of the invention, the co-network may contain from 1 to 99% by weight of functionalized synthetic polymer and between 99 and 1% by weight of functionalized protein.

In a particular embodiment, the co-network may contain from 70 to 30% by weight of functionalized synthetic polymer and between 30 to 70 t by weight of functionalized protein.

In another particular embodiment, the co-network may contain from about 50% by weight of functionalized synthetic polymer and about 50% by weight of functionalized protein.

In a particular embodiment, the co-network may contain from 70 to 80% by weight of functionalized synthetic polymer and between 30 and 20% by weight of functionalized protein.

In a particular embodiment, the material according to the present invention may contain from 5 to 20% in weight of functionalized synthetic polymer and from 5 to 20% in weight of functionalized protein.

In a preferred embodiment the material according to the present invention contains 5% in weight of functionalized synthetic polymer and 5% in weight of functionalized protein. In a preferred embodiment the material according to the present invention contains 10% in weight of functionalized synthetic polymer and 10% in weight of functionalized protein.

In a preferred embodiment the material according to the present invention contains 3% in weight of functionalized synthetic polymer and 7% in weight of functionalized protein.

In a preferred embodiment the material according to the present invention contains 7% in weight of functionalized synthetic polymer and 3% in weight of functionalized protein.

The protein to be functionalized may be of any origin such as human, animal, vegetal or bacterial origin.

In a particular embodiment, the said protein may be selected from the group consisting of albumin, globulin, lysozyme. The albumin may be human serum albumin or bovine serum albumin, or pig serum albumin. In one embodiment the serum protein is bovine serum albumin. In one particular embodiment the serum protein is human serum albumin.

In the context of the present invention, the grafting chemical groups X on the protein can be achieved by the covalent attachment of a functional chemical group to a side chain of amino acid of the protein thus creating a functionalized protein.

In a particular embodiment, the protein is grafted with functional groups X that are able to create chemical covalent bonds or bridges with other groups X when activated by the polymerization initiator, thus creating a network.

In an embodiment of the invention, the grafted chemical group X attached to the functionalized protein is the same as the grafted chemical group X attached to the functionalized synthetic polymer.

In one preferred embodiment, the grafted chemical group X attached to the protein is methacrylate. In one further preferred embodiment, the grafted chemical group attached to the synthetic polymer is methacrylate.

In a preferred embodiment, the present invention thus relates to a method of preparing a material as interpenetrating polymer network (IPN) associating a gel and a co-network of functionalized synthetic polymer cross-linked with a functionalized protein. In a preferred embodiment the protein is albumin (BSA or HSA) functionalized with methacrylate groups and the synthetic polymer is PVA functionalized with methacrylate groups. The material according to the invention is thus formed by a co-network of functionalized protein cross-linked with a functionalized synthetic polymer, that network is associated with a gel, particularly a fibrin gel, thus forming the IPN. There is no crosslinks between the gel, particularly the fibrin gel, and the co-network of functionalized protein and functionalized synthetic polymer.

The functionalization of the synthetic polymer by grafting of groups X can be achieved according to techniques known to the man skilled in the art. As a matter of example such a method for functionalization of PVA with X being methacrylate is one described in Biomacromolecules, DOI: 10.1021/bm400991k wherein the functionalization of PVA with methacrylate groups is described in detail. Particularly, PVA can be solubilized in DMSO with hydroquinone. 3 mol % 2-ICEMA (with respect to the hydroxyl function of PVA) can be added in the PVA solution. Reaction can therefore be mixed for about 4 h at about 60° C. and about 12 h at around 20° C. under argon atmosphere. The obtained solution is then purified by precipitation in acetone at room temperature. The modified PVA (denoted PVAm), i.e. functionalized synthetic polymer according the definition of the present invention, is thus filtered and dried under vacuum at 30° C. for 48 h before dissolution in Tris buffer 250 mM at pH 7.4.

The functionalization of the protein by grafting of group X can be achieved according to techniques known to the man skilled in the art. Protein can be solubilized in an adequate buffer such acid boric buffer 250 mM at pH 7.4 for example. Methacrylic acid N-hydroxysuccinimide ester (NHSm) solubilized in acetone can be added by drop wise up to a 0.7/1 molar ratio of NHSm/lysine of the protein. Reaction is carried out at room temperature for about 12 h in dark. Protein modified with methacrylate group, ie functionalized protein, can be purified by dialysis (Mcut off 1 kDa) against Tris buffer 50 mM at pH 7.4 in order to eliminate unreacted NHSm. In order to increase the functionalized protein concentration in solution, it is possible to lyophilize and to solubilize it at 20% (w/v) in Tris buffer 50 mM at pH 7.4.

In a preferred embodiment, the method according to the present invention comprises a method wherein the gel is a physical fibrin gel and the gel precursor solution is fibrinogen solution.

In another preferred embodiment, the method according to the present invention comprises a method wherein the gel is a physical fibrin gel and the gel precursor solution is plasma solution containing fibrinogen.

In a particularly preferred method according to the present invention the synthetic polymer is PVA and the grafted functional group X is methacrylate.

In a further preferred method according to the present invention the protein functionalized with at least one type of identical grafted chemical group X is a serum protein, particularly serum albumin functionalized with methacrylate. In another preferred method according to the present invention the gelification activator of the formation of the gel is thrombin and/or calcium.

In a further preferred method according to the present invention the step of incubating the reaction mixture obtained in i) or in ii) is achieved at a temperature comprised between 20° C. and 40° C., particularly 37° C.

In another embodiment of the invention, in the method according to the present invention the polymerization initiator is a photopolymerization initiator selected from the group consisting of Irgacures, particularly Irgacure 2959.

In a particularly preferred embodiment of the present invention, herein is provided a method for preparing a material as interpenetrating polymer network (IPN) associating a fibrin gel with a co-network of functionalized PVA crosslinked with a functionalized serum albumin, comprising the steps of:

i) preparing a first mixture by introducing into a buffer
   a. a fibrinogen containing solution,
   b. a functionalized synthetic polymer selected in the group consisting of polyvinyl alcohol (PVA) grafted with methacrylate,
   c. a functionalized serum albumin protein grafted with methacrylate
   d. a photopolymerization initiator, preferably Irgacure 2959,
ii) preparing a second reaction mixture by adding thrombin and/or calcium to the first mixture prepared in i),
iii) incubating the reaction mixture obtained in i) or in ii) at a temperature and during a time sufficient to allow formation of the gel, and
iv) performing photopolymerization and crosslinking reaction of the functionalized polyvinyl alcohol (PVA) grafted with methacrylate with the functionalized serum albumin protein grafted with methacrylate.

When the polymerization or reticulation is initiated, those functional grafted chemical groups X are able to create covalent bridges or bonds between functionalized synthetic polymers and functionalized proteins.

The polymerization initiator is a compound that generates free radicals. Any free radical generator known to the skilled person, for the polymerization, can be used.

For example, the initiator can be a thermal initiator selected from the group consisting of peroxides, persulfates, or diazo compounds, such as potassium persulfate, ammonium persulfate and hydrogen peroxide.

For example, the initiator may be a photopolymerization initiator. It may be selected from the group consisting of Irgacures (eg 2959, 184, 651, 819), 2-hydroxy-4-(2-hydroxyethoxy)-2-methylpropiophenone, benzophenone, 2-A dimethylbenzophenone, benzoin, benzophenone ion selected from the group comprising chloride trimethylmethylammonium benzophenone-4, the sodium salt of 4-sulfomethylbenzyl, aromatic ketones and aldehydes such as benzaldehyde, acetophenone, biacetyl, the parachlorobenzophenone, the ferulic acid, and all compounds producing radicals under visible or UV light. The Irgacure 2959 is preferably selected.

The concentrations of the different compounds in the mixture (step i) may be:
- if the gel is fibrin gel, then fibrinogen or plasma is used as gel precursor solution and the fibrinogen concentration may range from 1 to 50 mg/mL, preferably between 5 and 25 mg/mL
- the concentration of functionalized synthetic polymer, particularly PVA functionalized with methacrylate, may range from 1 to 400 mg/mL, preferably from 1 to 100 mg/mL
- the concentration of functionalized protein, particularly albumin functionalized with methacrylate, may range from 1 to 200 mg/mL, preferably from 1 to 100 mg/mL.

When thrombin is used as gelification activator in order to produce fibrin gel from fibrinogen solution or plasma in step ii), thrombin can be derived for example from human plasma or from pig or beef plasma.

The concentration of thrombin in the mixture of step (ii) can be for example 0.1 to 2.5 U/mL, preferably 0.2 to 1 U/mL. The concentration of calcium in the mixture of step (ii) can be for example from 5 to 50 mM, preferably 20 mM.
- the concentration of polymerization initiator, particularly Irgacure 2959, may range from 0.1 to 2 mg/mL, preferably of 0.6 mg/mL.

In step iii) the temperature of incubation can be a temperature allowing the formation of the gel this temperature may range for example between about 20 and 50° C., preferably, 30° C. to 40° C., more preferably around 37° C.

It is during this step iii) that the gel is formed from the gel forming solution or from gel forming precursor solution.

If the gel forming precursor solution is fibrinogen solution or plasma solution containing fibrinogen, it is during this stage, step iii) that the fibrin physical gel is formed from fibrinogen by enzymatic hydrolysis. The enzymatic hydrolysis is catalyzed by thrombin and calcium. Unexpectedly, the gel formation, the enzyme activity and the usual properties of the fibrin gel are not affected by the presence of functionalized synthetic polymer and of functionalized protein nor by their polymerization and reticulation. Moreover most of the properties, such as mechanical properties, of the fibrin gel are improved.

When the initiator is a thermal initiator, the polymerization of the functionalized synthetic polymer and functionalized protein can take place simultaneously with step (iii) or after step (iii). When polymerization takes place after step (iii), it can be implemented for example at a temperature between 25 and 60° C. Preferably the temperature is chosen such that the gel is not distorted. This is important when the gel is fibrin gel and precaution should be taken to avoid distortion of fibrin gel.

The thermal polymerization can be carried out between 0.5 and 10 hours, preferably between 1 and 3 hours in step iv).

When the initiator is a photopolymerization initiator, for example those mentioned above, the polymerization can be carried out in a UV/visible light at a wavelength between 190 and 800 nm, preferably under UV radiation of wavelength between 300 and 380 nm.

Photopolymerization in the step iv) may be performed for 30 minutes to 10 hours, preferably 30 minutes to 1 hour 30 minutes, even more preferably 1 hour.

The different solutions were prepared in Tris buffer or HEPES, preferably Tris-HCl at a concentration of 25 to 100 mM, preferably 50 mM, pH 7.2 to 7.5, preferably 7.4, containing $CaCl_2$ 10 to 50 mM, preferably 20 mM and NaCl 50 to 250 mM, preferably 150 mM.

The final concentrations of the different compounds in the mixture (step ii) may, for example:
- if the gel is fibrin gel, then fibrinogen solution or plasma is used as gel precursor solution and the fibrinogen concentration may range from 1 to 50 mg/mL, particularly between 2 and 25 mg/mL, more particularly between 1 and 10 mg/mL,
- for the functionalized polymers, particularly PVA functionalized with methacrylate, from 1 to 400 mg/mL, preferably around 100 mg/mL,
- for the functionalized protein, particularly albumin functionalized with methacrylate, from 1 to 200 mg/mL, preferably from 1 to 100 mg/mL,
- for the initiator 0.1 to 1 mg/mL, preferably 0.42 mg/mL, and
- for thrombin, if fibrinogen is used as gel precursor solution, of 0.1 to 2.5 U/mL, preferably 0.2 to 1 U/mL.

After step (iv), the method of the invention may further comprise a step of enzymatic crosslinking of physical fibrin gel. In this additional step can be used for example as transglutaminase or lysyl oxidase enzyme.

Transglutaminase is an enzyme which bridges covalently (or links) between them certain amino acids (primarily lysine and glutamine) which contribute to the crosslinking of proteins during the gelling process. This may well lead to a more resistant system having improved mechanical properties.

According to this embodiment, the enzyme transglutaminase for example, can be used. The IPN sample obtained after step (iv) is then immediately or subsequently immersed in a solution of transglutaminase in a concentration ranging from 0.1 to 10 U/mL, preferably between 0.5 and 3 U/mL for time variable from 5 minutes to 6 hours, preferably 30 minutes to 3 hours.

The method of the invention can be implemented in any container, beaker, crystallizer, pillbox, which can preferably be closed. The container can also be custom made with, for example, two glass plates or any UV transparent material and waterproof material. These plates may be separated by a Teflon gasket or polyethylene of various thicknesses of 100 mm to 3 mm, preferably 1 mm.

The invention also relates to the material in the form of interpenetrating polymer network (IPN) associating a gel, particularly a physical gel, more particularly a fibrin gel, with a co-network of functionalized polyvinyl alcohol covalently linked to a functionalized protein thank to methacrylate bridges, obtainable by the method according to the invention.

The material obtainable by the method according to the invention has the advantage of being in the form of a gel, homogeneous and self-supported while having dimensional stability over time.

It is thus an object of the present invention to provide a material obtainable by a method as herein described.

As mentioned above, in a preferred embodiment, the material of the invention is in the form of interpenetrating polymer network (IPN) combining a physical fibrin gel with a co-network of functionalized polyvinyl alcohol (PVA) crosslinked with functionalized protein, wherein there is no chemical bond nor covalent bonding between the fibrin gel component and the co-network components. In this interpenetrating polymer network (IPN), synthetic functionalized polymer and functionalized protein form a chemical network having a three-dimensional 3D existence. For example, PVA network may be synthesized by crosslinking poly(vinyl alcohol) modified with (meth)acrylate groups. PVA network swells in water or in the buffer. According to an advantageous embodiment of the invention, the material, the interpenetrating polymer (IPN) network combines physical fibrin gel and a network of polyvinyl alcohol prepared with poly(vinyl alcohol) functionalized with methacrylate, wherein the functionalized PVA is crosslinked to a functionalized protein. In one preferred embodiment the invention concerns a material as interpenetrating polymer network (IPN) associating a fibrin gel and a co-network of functionalized synthetic polymer crosslinked with a functionalized protein, wherein the functionalized protein is albumin functionalized with methacrylate groups and functionalized synthetic polymer is PVA functionalized with methacrylate groups.

The material according to the present invention shows improved properties compared to those of a sole fibrin gel. In particular mechanical properties, biodegradability and reversible dehydration and hydration properties are key features of the material according to the present invention. This is not the case for example for the fibrin gel alone which after a dehydration cycle, cannot rehydrate more than 25% of the initial value.

The material according to the present invention is self-supported and can be dehydrated in order to be stored and transported dried.

The material according to the present invention can thus be reversibly dehydrated and rehydrated. The material according to the invention can be dehydrated and then rehydrated between 25 and 100%, preferably between 45 and 95%.

Thus, in a particular embodiment of the present invention, here is provided a material according to the present invention which is dehydrated and has a moisture content of about 2 to 10% in weight, particularly about 2 to 5% in weight. The thus obtained dry material can be stored at room temperature and can be used upon necessity thank to extemporaneous rehydration within aqueous medium.

The drying of the material according to the invention can be achieved according to any technique known by the man skilled in the art and typically, the material can be disposed into an oven at a temperature comprised between 40 and 60° C. for a sufficient time to evaporate the contained water and to obtain a material with a moisture content of about 2 to 10% in weight, particularly about 3 to 5% in weight.

The material according to the invention has a glass transition temperature (Tg) between −100 and +100° C. and preferably between −50 and 80° C. The glass transition temperature Tg of a polymer material is defined as the temperature below which the polymer chains have a low relative mobility. Below Tg the polymer is in a glassy state, above Tg, the polymer is in a rubbery state. The glass transition temperature of a material can be measured, for example, by differential scanning calorimetry, DSC.

The material of the invention may also have a storage modulus (measured in shear mode, G') of between 100 Pa and 10 MPa, for instance between 1000 Pa and 6 MPa, in the hydrated state at 37° C. and a storage modulus (measured in voltage mode E') of between 0.01 and 3000 MPa, for example between 1 and 3000 MPa, in the dry state.

The module G of a material subjected to a sinusoidal strain is written in the complex form:

$$G^* = G' + iG''$$

i represents the imaginary part of a complex number.

In shear mode, the storage modulus of elasticity (G') is used to estimate the elasticity of the gel. The loss modulus or viscous modulus (G") characterizes the liquid phase of the gel. When G">G', the sample is regarded as liquid and when G'>G", the sample is considered as a gel. The gel time is considered as the time at which G' and G" moduli are equal.

The material obtainable by the method of the invention is preferably biocompatible. When one wishes to perform a sterile material synthesis (after the implementation of the method of the invention), the material is advantageously obtained by photopolymerization.

Another object of the invention is the use of a material according to the invention or obtainable by the method of the invention, such as:

Wound dressing,
Hemostatic dressing,
Surgical dressing,
A device for delivering therapeutic agents,
Coating for medical devices selected from the group consisting of stents, heart valves, catheters, vascular prosthetic filters,
Active carrier molecules selected from the group consisting of growth factors, antibiotics, bactericides, bacteriostats and enzymes,
Support for eukaryotic cells culture In a particular embodiment, the invention concerns the use of the present material as skin substitute in the treatment of burns and skin repair.

In another embodiment, the invention concerns the use of the present material as skin model for research and screening applications including penetration studies, pigmentation studies and toxicity, corrosivity and irritation testing, particularly in cosmetic.

Using functionalized protein such as serum albumin functionalized with methacrylate in addition to functionalized synthetic polymer such PVA functionalized with methacrylate, various IPN materials including a fibrin gel were obtained. The one pot-one shot method was applied in each case leading to a rapid synthesis (from 2 to 15 minutes). The mechanical properties of all IPN materials according to the present invention are sufficient to obtain self-supported IPN materials. The IPN architecture allows improving the storage modulus of the fibrin gel by a factor ranging from 8 to 40 depending on the IPN material composition. All materials are well synthesized and present interpenetrating polymer network architecture as shown by low soluble fractions. The protein based co-network (synthetic polymer, such as PVA, and protein such as serum albumin, both functionalized with methacrylate) is homogeneously spread.

The material according to the present invention is easily biodegradable due to the presence of the functionalized protein, particularly serum albumin, included and crosslinked with the functionalized synthetic polymer inside the material. This new type of material is the first co-network IPNs ever described in literature to be potentially biodegradable through fragmentation, then elimination within the biological environment, i.e. after implantation in the body. In addition, degradability helped to increase very significantly the bioactivity of materials.

Indeed, previously existing biomaterials are hardly biodegradable since they are made of synthetic polymers which are not easily degraded in situ by enzymes.

When functionalized protein, particularly serum albumin functionalized with methacrylate, is used as a constituent of the material according to the invention, the surface of the obtained material can be completely covered by fibroblasts within two weeks. In addition, cells at the surface of the material secrete the extracellular matrix biomacromolecules (fibronectin, hyaluronic acid) playing a key role in the early stages of wound healing and are able to structure them into fibers (fibronectin). The affinity properties of the molecules are identical to those of dermal fibroblasts (co-localization of fibronectin and hyaluronic acid). The good spreading of fibroblast cells on the surface of the materials allows them producing type I collagen which is a protein characteristic of late maturation phase. All these properties indicate that the materials according to the present invention are excellent supports for 2D-cell culture. Indeed, they could help to increase significantly the speed of wound healing. These innovative materials could therefore be used in their present state as dressings or to fill large defect of substance as they may be hydrolyzed and colonized progressively by surroundings cells. Moreover, they are also able to sustain 3D culture, so that they could be used to provide dermis in skin construct. The material according to the present invention is biodegradable by the action of endogeneous or exogeneous proteolytic enzymes may be stored dry and rehydrated without shrinkage upon desire.

In a preferred embodiment the use of serum albumin functionalized with methacrylate (BSAm or HSAm) copolymerized with PVA functionalized with methacrylate (PVAm) (co-network) into IPN architecture containing a fibrin gel allows the synthesis of a hybrid material with all the properties described above and biodegradable by enzymes, within the biological environment, i.e. after implantation in the body.

The material according to the present invention has been tested in contract with human cells, such as fibroblasts. It has been demonstrated that in addition to be non-cytotoxic, the material according to the present invention could be completely colonized by these cells. The development of a material according to the present invention with a homogeneous cellular distribution in the three dimensions of the material. constitutes an advantageous use of the present invention. Advantageously, the even distribution of cells within the whole matrix of the material according to the invention allows obtaining cellularized dressings or skin substitute. The living cells herein contained in the material of the invention will contribute to the reformation of the cellular matrix and wound healing by sustaining neoangiogenesis and the rebuilding of the burned, injured or damaged tissue.

A homogeneous distribution of cells, particularly fibroblasts, in three dimensions of a piece of material according to the present invention can be achieved through the encapsulation of a viable population of cells, particularly fibroblasts, which are thus embedded in the material. Cells cultured on the surface or encapsulated within the material according to the invention show a high viability as well as proliferation and matrix remodeling abilities.

It is thus a further object of the present invention to provide a material according to the herein described invention characterized in that it contains living cells encapsulated.

The encapsulation of cells in the material according to the present invention can support their viability for at least 5 weeks. Once encapsulated in the material of the invention, the cells slowly proliferate in the early phase of the culture, and their proliferative activity decreases after that early phase. The cells synthesize extracellular matrix components and are able to transform collagen type IV into collagen I. It is possible to freeze the material according to the present invention wherein living cells are encapsulated without losing viability and cell proliferative activity.

By the expression "encapsulated" used herein, it is to be understood that the cells are evenly distributed with the whole matrix of the material according to the invention in the three directions.

It is thus an object of the present invention to provide a material according to the present invention characterized in that it contains encapsulated living cells.

The encapsulation of cells within the material according to the present invention may be achieved by the addition of cells suspension to the first reaction mixture as herein described.

In a particular embodiment the method of the present invention for the preparation of a material according to the present invention further comprises the step of adding a cell suspension in the first mixture, prior to the step of introduction of polymerization initiator.

The quantity of cells added in the first reaction mixture is such that the final quantity of cells with the material is comprised between $1*10^6$ and $3*10^6$ cells per unit of gel material obtained. A unit of gel may have any form or size and would typically have the size and the shape of the mold used for its manufacture. A unit may thus be a cylinder, a cube or a parallelepiped for example which dimension will be dependent upon the intended use.

The encapsulation of cells such as fibroblasts can be achieved by adding the so called first mixture containing the gel forming solution or gel forming precursor solution with functionalized synthetic polymer, functionalized protein, polymerization initiator, particularly a photopolymerization initiator, to a cell suspension. The resulting solution was placed in a mold and then exposed to UV for the synthesis of IPN as exposed above. The obtained material is then immersed in a culture medium at 37° C. for sufficient time to remove traces of synthesis buffer. The density of cells obtained is dependent upon the concentration of cells in the suspension which can be chosen in order to obtain a final density of about 1000 to 10000 cells/$mm^3$, particularly between 4000 and 8000 cells/$mm^3$; more particularly around 7000 cells/$mm^3$.

It is particularly noticeable that the photopolymerization under UV does not affect the viability of cells embedded with the material of the invention. U.V exposure does not cause mortality of cell on the surface not within the material. After 1 and 3 weeks of culture, cell population is at least maintained and the distribution remains homogeneous. In addition, the cells initially present on the surface are strongly expanded and do cover the material. This distribution on the one hand, and the lack of mortality on the other hand, confirms that there is no impact of UV exposure on the cell population comprised on and within the material encapsulating cells.

Cell count shows an overall increase in cell population with the cultivation time. Indeed, after three weeks, the cell population is 150% of the initial value. Thus, even if the cells ace encapsulated in a matrix comprising the functionalized PVA coreticulated with functionalized protein, they are able to proliferate within the material.

As a matter of example for material containing cells embedded within it, as it is observed with cell culture onto the material of the invention, fibronectin is present at 24 hours of culture. Between 1 and 3 weeks of culture, a significant increase in the presence of fibronectin is visible on the depth of the material. After 3 weeks of culture, different protein structures are observed depending on depth studied. Indeed, on the surface, fibronectin adopts a typical fibrillar form indicating that the protein has been remodeled and integrated into the matrix. In depth, fibronectin is located around the cells. All of these results suggest that it is possible to produce cellularized dressings by encapsulation of fibroblasts within a material according to the invention. This type of material would be able to promote wound healing and secretion of extracellular matrix macromolecules such as fibronectin and collagen. The possibility of encapsulating living cells within the material of the invention and the capacity of the cells to proliferate in it makes this material capable of being used as a cellularized skin substitute for the treatment of burns for example.

It is also noticeable that the material according to the invention containing encapsulated cells can be frozen, kept frozen and defrosted without alteration of the viability of the cells embedded in it. The viability of the cells encapsulated are not affected by freezing at −80° C. and the material of the invention containing encapsulated cells can be stored in the frozen state at −80° C. for several months without alteration of the contained cells that can restart their growth once the material is unfrozen. Typically the cryopreservation of encapsulated cells is achieved by traditional means known by the man skilled in the art. A material containing cells encapsulated according to the present invention is incubated in fetal bovine serum for few hours with or without cryoprotectant such as glycerol prior to freezing at −80° C. during few hours. The material of the invention containing encapsulated cells can then be stored at −80° C. for months. The thawing is preferably achieved by a rapid warming of the frozen sample, for example by incubation A 37° C. The defrosted material containing encapsulated cells can be cultivated under classical conditions and the cell viability, proliferative activity as well extracellular protein production is not affected.

It is thus a further object of the present invention to provide a material according to the invention that can contain encapsulated cells and that is frozen.

The material according to the present invention, IPN containing a fibrin gel scaffold at physiological concentration and a co-network of functionalized synthetic polymer crosslinked with a functionalized protein, has excellent properties that make it suitable to be used as wound dressings or cell culture support or matrix for skin regeneration. In addition, thanks to the ability of the material according to the invention to encapsulate cells, particularly fibroblasts, such a material based on co-network of PVA functionalized with methacrylate and albumin functionalized with methacrylate, particularly serum albumin functionalized with methacrylate, makes it suitable as a skin substitute in the treatment of burns and skin repair.

It is thus a further object of the present invention to provide the use of a material according to the present invention as a skin substitute in the treatment of burns and skin repair.

The material of the invention can be used as hemostatic dressing. In case of bleeding, platelets aggregate on fibrin, release growth factors of coagulation factors leading to blood thrombus organization. The material according to the present invention is biodegradable and can thus serve as support for cell culture. Also, in the case of loss of ground substance as can occur upon severe burning, the material according to the present invention can stimulate angiogenesis and can thus sustain the rebuilding of the affected tissues.

The material according to the present invention exhibits very good rehydration properties after dry storage, as well as enzymatic degradation by proteases once in place. The material allows the maintenance of a humid atmosphere for the wound and cell growth on the surface and the secretion an extracellular matrix. The material according to the present invention is able to support and sustain the reformation of normal tissue at the wound sites.

Other advantages may also occur to those skilled in the art upon reading the following examples, illustrated by the accompanying drawings, given by way of illustration.

EXAMPLES

Materials and Methods

Chemicals

Figure 1:
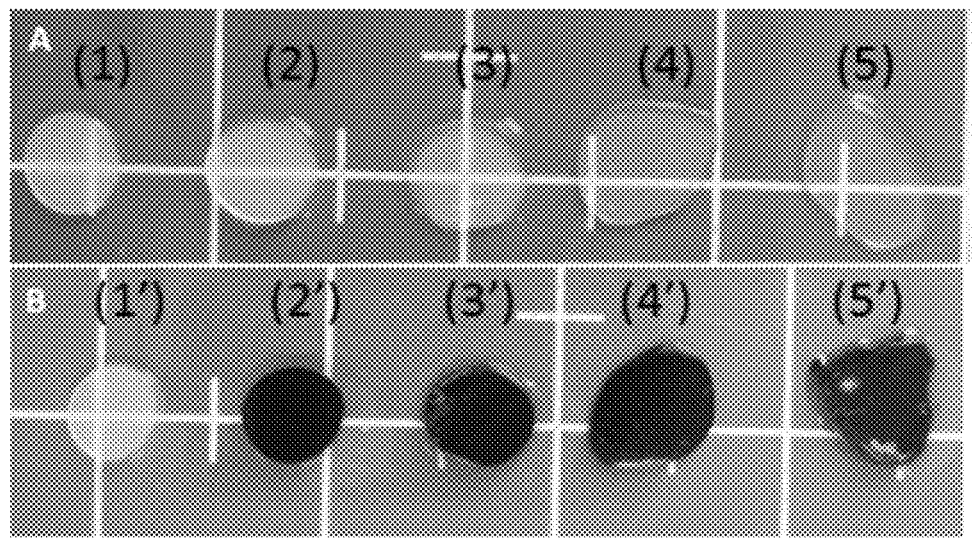
FIG. 1 shows:
A—Hydrogel IPNs (1, 2, 3, 4, 5) just after synthesis with respectively 0, 3, 5, 7 and 10% (w/v) of BSAm and supplement with PVAm to a final 10% (w/v) concentration.
B—Hydrogel IPNs (1, 2, 3, 4, 5) after coloration with Coomassie blue, respectively (1', 2', 3', 4', 5').

Thrombin (BP 25432), sodium chloride, sodium dodecylsulfate, were purchased from Fisher Reagents and bovine fibrinogen (Fg—341573) from Calbiochem. Tris(hydroxymethyl)aminomethane were purchased from VWR. Calcium chloride and magnesium chloride were obtained from Riedel-deHaën and Prolabo, respectively. Azide, Brillant Blue R, sodium carbonate, dietholamine, 2-isocyanatoethyl methacrylate (2-ICEMA), paraformaldehyde (PFA, P-6148), 4,6-diamino-2-phenyl-indole (DAPI, D-9564), albumin from bovine serum (purity≥98%, A7906), methacrylic acid N-hydroxysuccinimide ester (purity=98%, 730300), thermolysin from *Bacillus thermoproteolyticus* rokko (P1512), anti-human fibronectin IgG (produced in rabbit, F3648) and alkaline-phosphatase conjugated anti-rabbit IgG (A3687) were obtained from Sigma. Anti-fibrinogen from rabbit (A0080) was obtained from Dako. P-nitrophenyl phosphate (pNPP, 71768) was purchased from Fluka. Anti-human type I collagen IgG (produced in mouse, MAB3391) and anti-human hyaluronic acid IgG (produced in sheep, AB53842) were purchased respectively from Millipore and Abcam. Polyvinyl alcohol (PVA 98%, M=16000 g/mol) and hydroquinone were purchased from Acros. 2-hydroxy-1-[4-(2-hydroxyethoxyl)phenyl]-2-methyl-1-propanone (Irgacure—12959) was purchased from Ciba. Acid boric and dimethylsulfoxide (DMSO) were purchased from Merck. DMSO was dried before utilization and stored in the dark on molecular sieve under argon. Phalloidin-Alexa® 532 (P-5282), Alamar blue (DAL 11000) and LIVE/DEAD® kit (L3224) were obtained from Invitrogen. Immunoglobulin (IgG) against mouse (produced in goat, A11029), sheep (produced in donkey, A11057) and rabbit (produced in goat, A21071) labeled respectively with Alexa® 488, 568 and 633 were also obtained from Invitrogen. Penicillin-streptomycin (1416), culture medium DMEM high glucose (31966021), Trypsine EDTA, and FBS (foetal bovine serum, 10270-106) were obtained from Gibco.

Synthesis of Polyvinyl Alcohol (PVAm) Modified with Methacrylate Groups

PVA was modified with methacrylate groups as described. Briefly, 20% (w/v) PVA was solubilized in DMSO with hydroquinone. 3 mol % 2-ICEMA (with respect to the hydroxyl function of PVA) were added in the PVA solution. Reaction was mixed for 4 h at 60° C. and 12 h at 20° C. under argon atmosphere. This solution was purified by precipitation in acetone at room temperature. The modified PVA (denoted PVAm) was filtered and dried under vacuum at 30° C. for 48 h before dissolution in Tris buffer 250 mM at pH 7.4. Tg of PVAm is 75° C.

Synthesis of Bovine Serum Albumin (BSAm) Modified with Methacrylate Groups

4% (w/v) BSA were solubilized in acid boric buffer 250 mM at pH 7.4. Methacrylic acid N-hydroxysuccinimide ester (NHSm) solubilized in acetone was added by drop wise up to a 0.7/1 molar ratio of NHSm/lysine of BSA. Reaction was carried out at room temperature for 12 h in dark. BSA modified with methacrylate groups (denoted BSAm) was purified by dialysis (Mcut off 1 kDa) against Tris buffer 50 mM at pH 7.4 in order to eliminate unreacted NHSm. To increase the BSAm concentration in solution, it was lyophilized and solubilized at 20% (w/v) in Tris buffer 50 mM at pH 7.4. Solution of BSAm was filtered (0.22 µm, Millipore) before storage (−20° C.).

Gelation Procedure

All reactants were solubilized in a 0.05 mol/L Tris-HCl buffer pH 7.4 and incubated at 37° C. for 15 min prior to mixing. Same protocol was used for any materials regardless of PVAm and BSAm ratio.

Co-network/Fibrin IPN was synthesized as follows: 1 mL of Tris-HCl buffer containing 10% (w/v) of polymers (PVAm 10%, PVAm(5%)coBSAm(5%), PVAm(3%)coBSAm(7%) and BSAm 10%), 5 mg fibrinogen, 0.20 units thrombin, 0.15 mol/L NaCl, 0.02 mol/L CaCl$_2$, 0.0424 (w/v) Irgacure 2959 was prepared in a microvial. The mixture was placed into mold made by Teflon® and glasses. The mold was placed at 5 cm from a IUV lamp (VL-6, Bioblock, 2×5W, 365 nm) for 1 h at 37° C. Self-supported materials were obtained with areas varying from 1.5 to 78.5 cm$^2$, according to the mold size.

Soluble Fraction

Soluble fraction of synthetic polymer networks was extracted for 48 h in Soxhlet with deionized water. The samples were weighted before ($w_i$) and after ($w_f$) and soluble fractions were determined as follow:

$$SF(\%)=[(w_i-w_f+w_{salt})/(w_i)]*100$$

Unreacted fibrinogen in IPNs was extracted by immersion of materials in a 10-fold volume of buffer during one night. Concentration of protein extracted from hydrogels was assessed by Elisa test. Absorbance was detected with a plate reader (Bio Tek) at 405 nm. Each sample was synthesized in triplicate, and each measurement repeated three times.

Staining of Materials by Coomassie Blue

PVAm(10%) and BSAm(10%) single networks and co-networks containing PVAm and BSAm at different ratios were incubated for 1.5 h in aqueous coloration solution containing 2.5% (w/v) Coomassie blue, 40% (v/v) ethanol, and 7% (v/v) acetic acid. Then, the materials were rinsed in aqueous solution containing 20% (v/v) ethanol and 10% (v/v) acetic acid until removing of excessive coloration was done.

Rheology

Gelation study was performed by Rheological measurements with an Anton Paar Physica MCR 301 rheometer equipped with CTD 450 temperature control device with cone-plate geometry (cone: diameter 25 mm, angle 2°; plate: polymerization system made from glass coupled with U.V Source Omnicure). The solution of precursors of materials was put between the two geometry and measurements begin immediately. Polymerization was initiated by U.V exposure (4.46 mW/cm$^2$) at 37° C. Storage modulus (G') and loss modulus (G") at 1% deformation imposed at 1 Hz were recorded as a function of time. The final storage modulus G' is determined after 1 h UV exposition (system equilibrium reached) and gel time was determined at the intersection between storage and loss modulus curves. The average values of the shear modulus were measured 3 times minimum.

Enzymatic Degradation of Materials

Just after synthesis, materials were immersed in Tris Buffer 50 mM pH 7.4, 0.02% (w/v) $NaN_3$ containing 20 U/mL thermolysin. The hydrolysis volume solution is 20 fold the volume of the materials. Enzymatic degradation of the materials was performed at 37° C. for 24h.

BSAm and Fb Repartition.

Proteins in BSAm based IPN are specifically labeled as follows. After synthesis, materials are immersed in PBS-casein buffer for 1 h at 37° C. before incubation first in PBS buffer with 1%(w/v) casein containing BSA-antibodies (1/50) for 1 h at 37° C. After 3 successive rinses in PBS buffer, they are then incubated in PBS-casein buffer containing secondary rabbit-antibodies 350 (1/100) for 1 h at 37° C. Finally, fibrin specific staining is performed in PBS-casein buffer containing FITC fibrin-antibodies (1/100) for 1 h at 37° C., followed by 3 successive rinses before confocal microscope observation with a ×63 (Plan-Apochromat 63×/1.4) objective.

Biocompatibility Test

Cell Culture

Cell line used for biocompatibility test was Human fibroblast from foreskin (FB-BJ, ATCC CRL 2522). All cells were cultured in DMEM high glucose medium supplemented with 10% (v/v) fetal bovine serum (FBS) and penicillin-streptomycin in a humidified 5% $CO_2$ incubator. All experiments were performed with cell between 9 to 11 scans after de-freezing of ATCC vial.

Cell Seeding

For cell seeding on surface of materials, they were placed in a sterile culture plate (P24) and immersed in 1 mL of culture medium without FBS for at least 24 h. They were then seeded with 1 mL of a cell suspension containing $1 \times 10^5$ cell/mL (cell density $5 \times 10^4$ cell/$cm^2$). The materials tested in triplicate at different culture times (from one day to 3 weeks) were the BSAm(10%) single network, PVAm(5%)coBSAm) (5%)/Fb IPN, PVAm(3%)coBSAm(7%)/Fb IPN and BSAm (10%)/Fb IPN.

Live/Dead® Assay

Viability tests were performed by staining cells with a solution containing 0.2 μM calcein AM and 0.2 μM ethidium bromide dimer in phosphate buffer for 30 min at 37° C. Picture were taken with Confocal Laser Scanning Microscope (CLSM, Zeiss LSM 710, Germany) in sequential line mode (averaging 2) with a ×10 (EC Plan-Neofluar 10×/0.30 M27) objective. Living and dead cells were stained respectively with calcein AM ($\lambda ex$=488 nm, $\lambda em$=490-573 nm) and ethidiumbromide dimer ($\lambda ex$=561 nm, $\lambda em$=580-730 nm). Evaluation of cell population was performed using ImageJ® software (Cell counter plug in) and viability of cell were calculated by the formula:

% Viability=[(full population of cell−quantity of dead cell)/(full population of cell)]*100

Cell Staining

A particular attention has been paid to the origin of antibodies and to the emission wavelength of conjugated dyes, so that 5 different stainings have been performed on every sample to allow direct observation of cell morphology and ECM remodeling at the same time.

Cell fixation was carried out with 3% (w/v) paraformaldehyde solution for 12 h at 37° C., permeabilized with a PBS-0.1% (v/v) Triton X-100 solution at room temperature (RT) for 30 min and rinsed with PBS. Then non-specific binding sites were blocked by immersion in saturation buffer composed of PBS with 10% (v/v) FBS for 30 min at room temperature.

For cell density studies, nuclei were stained with DAPI (1 μg/mL) for 1 h at room temperature and then rinsed. Cells were observed with CLSM with a ×20 (Plan-Apochromat 20×/0.8 M27) objective. Cell numbers were quantified by counting nuclei with ImageJ® software (Cell counter plug in).

For cell morphology and ECM remodeling studies, primary antibody solutions against human collagen, hyaluronic acid and fibronectin were deposited on the surface of materials. After 45 min incubation at room temperature, samples were rinsed and labeled for 45 min with a staining solution containing DAPI (1 μg/mL), phalloidin Alexa® 532 (dilution 1/10000) and secondary antibodies. Materials surfaces were observed with CLSM with a ×20 (Plan-Apochromat 20×/0.8 M27) objective.

Results and Discussion

The aim of this work is to introduce a biodegradable part inside a synthetic polymer network incorporated into a fibrin-based Interpenetrating Polymer Networks (IPN) architecture to insure the progressive vanishing of the material.

Serum albumin was chosen as the biodegradable part as it is the major proteic component of serum, the same biological source as fibrinogen. Moreover, due to its polypeptide nature, serum albumin is naturally responsive to various proteases. Bovine serum albumin (BSA) was grafted with methacrylate groups to be able to generate a network—or to copolymerize with another polymer precursor—through photopolymerization. An average of 66% free amine groups of BSA, mainly located on the lateral chains of lysine residues, was modified with a methacrylate group after the procedure. The modified protein, named BSAm, was synthesized with a 91% yield.

BSAm Single Networks and PVAm-BSAm Co-Networks

First the possibility to generate BSAm and PVAm-coBSAm homogeneous networks was explored. BSAm is used to confer biodegradability to the network and PVAm to provide good mechanical and hydration properties to the biomaterial. In order to maintain favorable conditions for the further formation of a fibrin network, the synthesis was carried out in buffer pH 7.4 with appropriate salt concentration. Irgacure 2959 was selected as photoinitiator because it is well known to be weakly toxic and noxious towards different types of cells at concentrations lower than 0.1% (w/v); the concentration here used is 0.04%.

Under these conditions, different homogeneous materials were obtained with BSAm concentration ranging from 0 to 10 wt %, the final polymer concentration (BSAm+PVAm) being 10 wt % in all cases. The higher the BSAm ratio, the more transparent they are (FIG. 1A).

It may also been observed that with a low concentration (3%, A-4) or in the absence (A-5) of PVAm, the network deforms and the initial regular round shape is not maintained after removing the mould.

After their synthesis, the proteins in the different co-networks were stained with Commassie blue. As shown in FIG. 1 B, the coloration of the different materials containing BSAm is regular, indicating a homogeneous repartition of proteins (BSAm) inside the materials. The absence of coloration with PVAm alone ascertains the method validity.

Having shown that a single BSAm network and various BSAmcoPVAm co-networks may be obtained, materials including a fibrin gel in IPN architecture were synthesized. BSAm/Fibrin and PVAm—BSAm/Fibrin IPNs The free radical photopolymerization of the BSAm and PVAm, initiated by U.V exposure, was performed in aqueous buffered medium at 37° C. all along with the fibrin gel formation that was synthesized by the enzymatic hydrolysis of fibrinogen by thrombin. Using the same conditions, the in situ syntheses of BSAm(10%)/Fb IPN and of various PVAmcoBSAm/Fb IPNs have been developed. The precursor solutions contain fibrinogen and 10% methacrylate polymers (BSAm+PVAm) with BSAm concentrations being 0, 5 or 10% (w/v).

In all cases, a material was obtained after 15 min. The presence of fibrinogen has no significant impact on the formation rate of the synthetic networks as gelation occurs at similar times for single co-networks and IPNs.

After 60 min irradiation, the storage moduli were measured and those for IPNs compared to that obtained for the fibrin network. All materials containing either BSAm or/and PVAm are self-supported (G'>100 Pa) both as single co-networks and in IPN architectures. The addition of any synthetic network to a fibrin gel improves its mechanical properties as shown by the large increase in storage modulus (G') from 8 to 40 fold. The synthetic networks well fulfill their role of rendering a fibrin gel easily handled. As suggested above through the visual observation, the single BSAm network shows lower mechanical properties (G'=220 Pa) than co-network with 5% PVAm (G'=830 Pa) or than the PVAm single network (G'=3160 Pa). However, the addition of the fibrin gel improves this characteristic a lot (from 220 to 868 Pa).

To check the effective formation of the co-networks in IPN architecture, extractions of both the synthetic and the fibrin fractions of the materials were performed.

Figure 2:
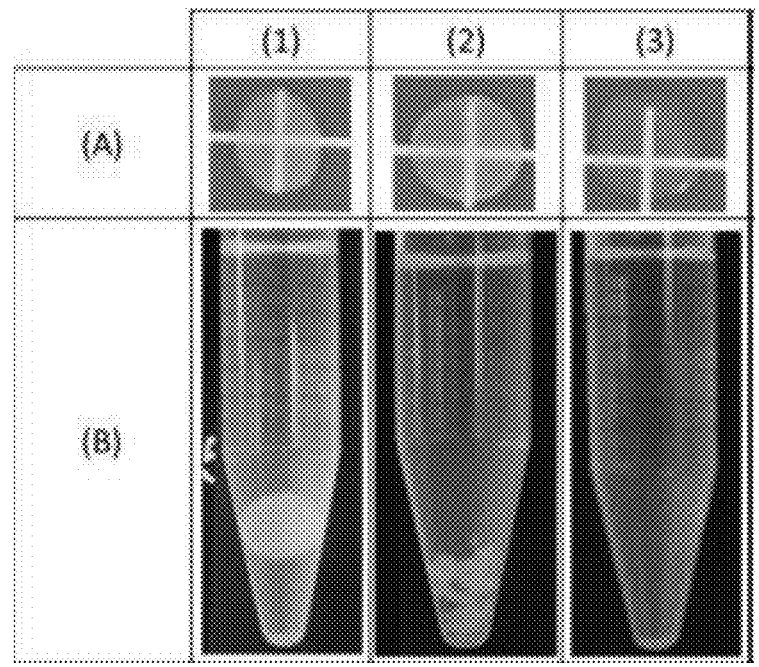
FIG. 2 shows (1) PVAm(10%)/Fb; (2) PVAm(5%)coBSAm(5%)/Fb; (3) BSAm(10%)/Fb IPNs (A) just after synthesis and (B) after 24 h incubation in a thermolysin solution (20 U. mL$^{-1}$) at 37° C.

To check the effective formation of the networks in IPN architecture, extractions of both the synthetic and the fibrin fractions of the materials were performed. The results are presented in Table 1.

was thus tested. The different IPNs were incubated with a concentrated metalloprotease solution. The results are illustrated in FIG. 2-B.

As suspected, the PVAm(10%)/Fb IPN is not solubilized by the protease under those conditions. Thermolysin may degrade the fibrin network inside the IPN, but this protein represents only 5 wt % of the solid fraction of the IPN, so its proteolysis does not lead to the dislocation of the material. This experiment also proves the good repartition of PVAm inside the IPN architecture as the round shape of the material is not affected by the hydrolysis of the fibrin network. This point illustrates one of the best properties of the material here generated; its shape stays constant, even in presence of degrading enzymes.

The PVAm(5%)coBSAm(5%)/Fb IPN is partly degraded upon enzyme action; many fragments are obtained, indicating that BSAm was also well distributed in the co-network.

The BSAm(10%)/Fb IPN is totally degraded by the protease. This material is thus well biodegradable. A similar result may be obtained with a lower enzyme concentration (10 U/mL).

Figure 3:
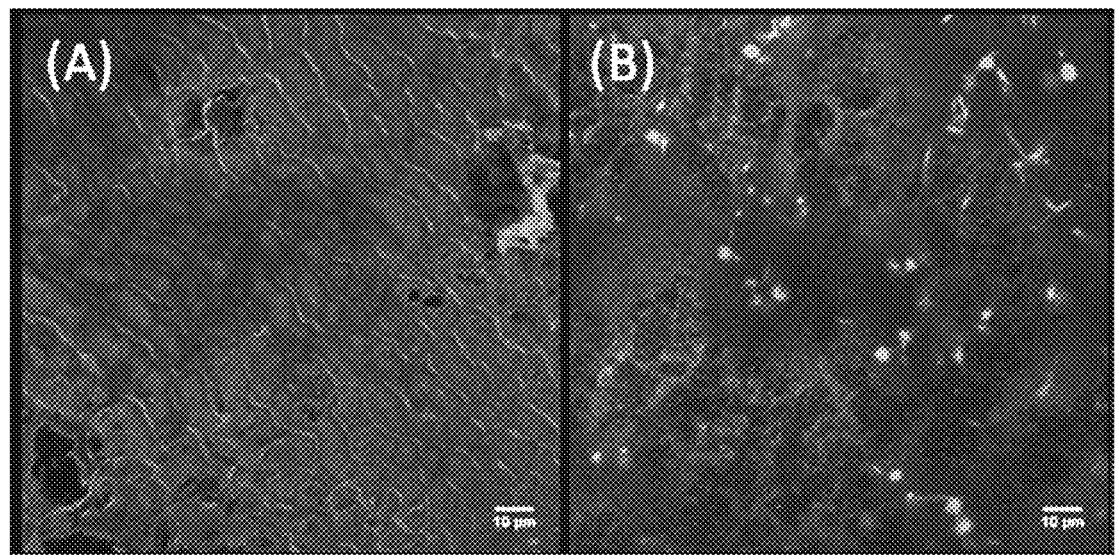
FIG. 3 shows observation by confocal microscopy of the repartition of BSAm and fibrin Fb (both light grey) in a BSAm(10%)/Fb IPN (A) and in PVAm(5%)coBSAm(5%)/Fb IPN (B). —Objectif x63
Figure 4:
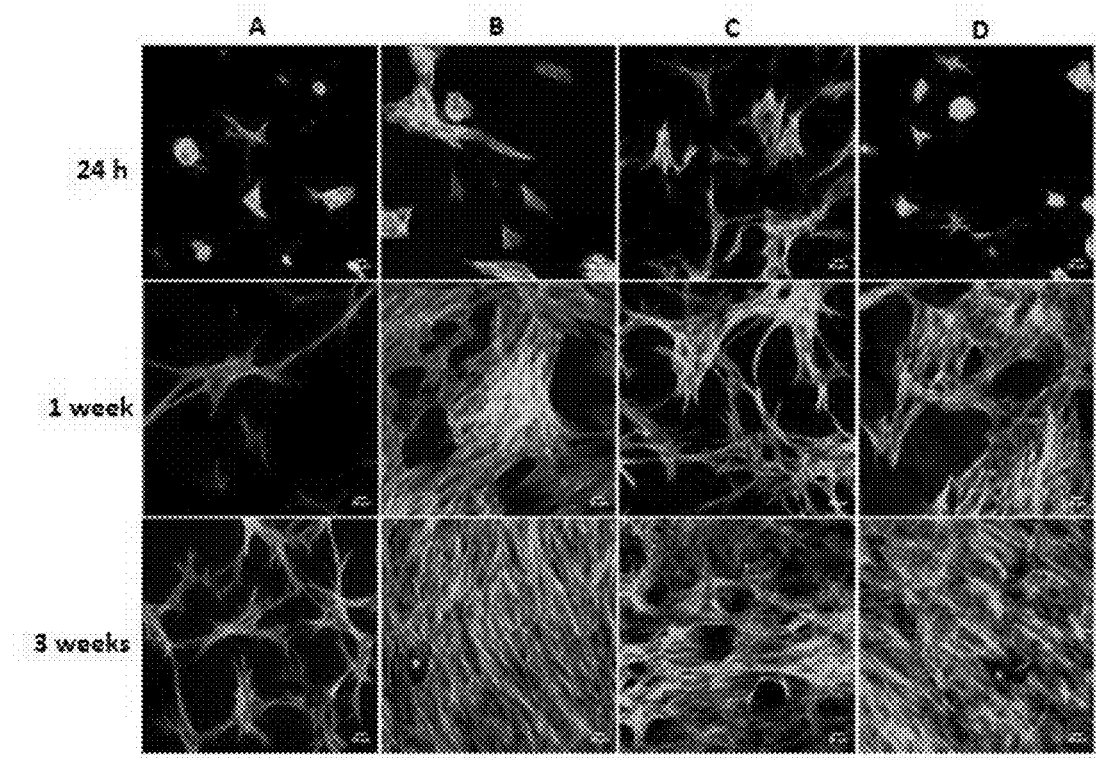
FIG. 4 shows cell morphology with cytoskeleton and nucleus, after 1 day, 1 and 3 weeks of culture on BSAm (10%) single network (A) and PVAm(5%)coBSAm(5)/Fb (B), PVAm(3%)coBSAm(7%)/Fb (C) and BSAm(10%)/Fb (D) IPNs. Cells were observed with a x20 objective by CLSM (Zeiss LSM710). Scale bar: 20 μm.

These experiments show that BSAm in the material is well accessible to the protease and may be hydrolyzed even in the IPN architecture. The homogeneous repartition of BSAm in the BSAm(10%)/Fb IPN and in the PVAm(5%)coBSAm(5%)/Fb IPN has been imaged in confocal laser scanning microscopy using specific fluorescent probes for both proteins (FIG. 3).

Staining of the BSAm(10%)/Fb IPN with antibodies reveals an homogeneous repartition of BSAm in the whole material. Moreover, the fibrin network observed in the BSAm(10%)/Fb IPN presents the characteristic honeycomb structure of a single and biologically active fibrin network.

TABLE 1

Soluble synthetic and fibrin fraction for various single networks, IPNs and fibrin gel.

| Sample | SN PVAm | IPN PVAm/Fb | IPN PVAmcoBSAm/Fb | IPN BSAm/Fb | SN Fb |
|---|---|---|---|---|---|
| % soluble synthetic fraction | 8% ± 0.3 | 12% ± 2 | 16% ± 0.9 | 16% ± 5 | / |
| % sosluble fibrin fraction | / | 0.18% ± 0.22 | 0.47% ± 0.03 | 0.32% ± 0.03 | 0.03% ± 0.03 |

From the Soxhlet extraction, it appears that the part of methacrylate polymers which is not included in the synthetic network varies from 12 to 16 wt %. These values are high but correct for polymer networks synthesized from a diluted precursor solution.

The proper formation of the fibrin network was also verified. The Elisa assay on extraction solution of IPNs shows less than 1 wt % of extractable fibrinogen whatever the composition of its partner network. These results confirm that the synthetic network does not inhibit the enzymatic formation of fibrin network by thrombin. Using a Western blot technique after disruption of the IPNs, the presence of an intense γ-γ band was also evidenced, confirming the transformation of fibrinogen into fibrin upon thrombin cleavage and the association of fibrin chains into a gel phase inside the material.

Biodegradability

Next, PVAm(10%)/Fb, PVAm(5%)coBSAm(5%)/Fb and BSAm(10%)/Fb IPNs were synthesized and observed (FIG. 1, A). As for the single networks, the BSAm/Fb IPN (A-3) is more transparent than IPNs containing PVAm (A-2 and A-1). Accordingly to the rheology results, the three materials keep their round shape just after synthesis. Their degradation This indicates that the increase in gel time due to the presence of BSAm (from 3 to 15 minutes) is not related to a perturbation in the fibrin network formation.

For the PVAm(5%)coBSAm(5%)/Fb IPN, BSAm is also present in the whole volume while fibrin forms larger connected fibrils forming an irregular network.

However, both proteins are present throughout the material. Combination of all the results: similar extract concentrations with a Soxhlet for a BSAm or a PVAmcoBSAm network in the IPNs, homogeneous coloration with coomassie blue, homogeneous repartition of BSAm in all the IPNs, increase of mechanical properties and homogeneous biodegradability suggest that photopolymerization successfully formed a copolymer between PVAm and BSAm.

Material Made with Plasma

Blood plasma from the Etablissement Français du Sang (EFS) filtered through 0.22 microns, or not filtered, was used as a source fibrinogen.

The protocol includes solubilizing PVAm in Tris buffer, followed by addition of plasma instead of fibrinogen and the formation of IPN is similar to the protocol used in the previous examples. In all cases, calcium (20 mM) and thrombin (0.2 U/mL) were added to enable the rapid formation of the fibrin network.

IPN containing co-network of PVAm and HSAm as well as a fibrin gel from plasma were synthesized according to the same principle as in the previous examples. In this case, the lyophilized HSAm is dissolved in the plasma, in order to have the concentration as high as possible (2.8 mg/mL) of fibrinogen. These materials are homogeneous and can be manipulated. Obtained synthetic materials are homogeneous and translucent. Following incubation in the Coomassie Blue and successive rinses, the IPN made with plasma has a uniform blue color. This indicates that the fibrin network is homogeneously distributed in the materials. On extractable protein, the single network PVAm (10%) and PVAm (5%) coHSAm (5%) co-network have zero values, thus constituting robust negative control and in the case of the PVAm (10%)/plasma IPN and co-network PVAm (5%) coHSAm (5%)/plasma IPN, soluble fractions are less than 0.1%: the fibrin network is well formed, and the presence of PVAm and HSAm does not alter its formation. As regards to rheological characteristics as previously measured, the module of co-network PVAm (5%) coHSAm (5%)/plasma IPN is 61 Pa (38 Pa for the co-network PVA (5%) co HSAm (5%)/Fb IPN.

The use of plasma instead of fibrinogen seems to increase the storage modulus.

Regarding biodegradability: PVAm (10 m)/plasma IPN retain its integrity after being incubated in the enzyme solution of thermolysin. The co-network PVAm (5%) coHSAm (5%)/plasma IPN was completely degraded in the enzyme solution. The feasibility and biodegradability of the plasma based IPN co-network materials according to the invention have been verified.

Material Cytotoxicity

The impact of these different materials on fibroblast viability, proliferation and their extracellular matrix synthesis was explored. A cell suspension (50 000 cells/cm$^2$; confluent density) is put in contact with the PVAm(5%) coBSAm(5%)/Fb, PVAm(3%)coBSAm(7%)/Fb and BSAm (10)/Fb IPNs and with BSAm(10%) single network as controls. After incubation between 24 h and 3 weeks, a metabolic assay (Alamar Blue®, supplementary data) shows no alteration of metabolic activity in comparison with the control. Then cells were imaged by confocal microscopy to determine their morphology and their density on the materials. Finally, the proportion of dead cells was assessed (Live/Dead test) to conclude on the biocompatibility of these different materials.

First the cell morphology was observed. Nuclei and actin cytoskeleton were stained with DAPI and phalloidin, respectively.

Whatever the material, cell morphology evolves over time. After 24 h culture on the single BSAm(10%) network or on BSAm(10%)/Fb IPN, cells are round or star shaped. After 1 to 3 weeks of culture on the BSAm(10%) single network, all cells are elongated but show little spreading and many pseudopodia. The cytoskeleton shows many stress fibers. Thus, cells do not easily adhere on this network surface on which they do not acquire their normal fibroblast morphology and do not proliferate much. During the same time, cells are much more spread on the BSAm(10%)/Fb IPN where they tend to adopt a stellate morphology. Their cytoskeleton is visible with coarse stress fibers and a substantial increase of the cell population is observed during the 3 weeks of culture. The introduction of fibrin into the BSAm network (BSAm(10%)/Fb IPN) allows fibroblasts to spread, to increase their cell surface and to proliferate up to total recovery of the material surface. Cells do not spread and grow on PVAm single network. Adding fibrin (PVAm(10%)/Fb IPN) improves the cell viability but does not allow an important cell growth. On the contrary, when PVAm is copolymerized with BSAm in an IPN architecture containing fibrin (PVAm(5%)coBSAm(5%)/Fb and PVAm(3%) coBSAm(7%)/Fb IPNs), cells are plated after 24 h of culture. After 1 and 3 weeks, the cells are already polarized and adopt the typical fusiform fibroblast morphology. The cytoskeleton fibers are also clearly visible. Cell populations are almost confluent after the first week of culture and the whole material surface is covered uniformly by cells after 2 weeks of culture.

Figure 5:
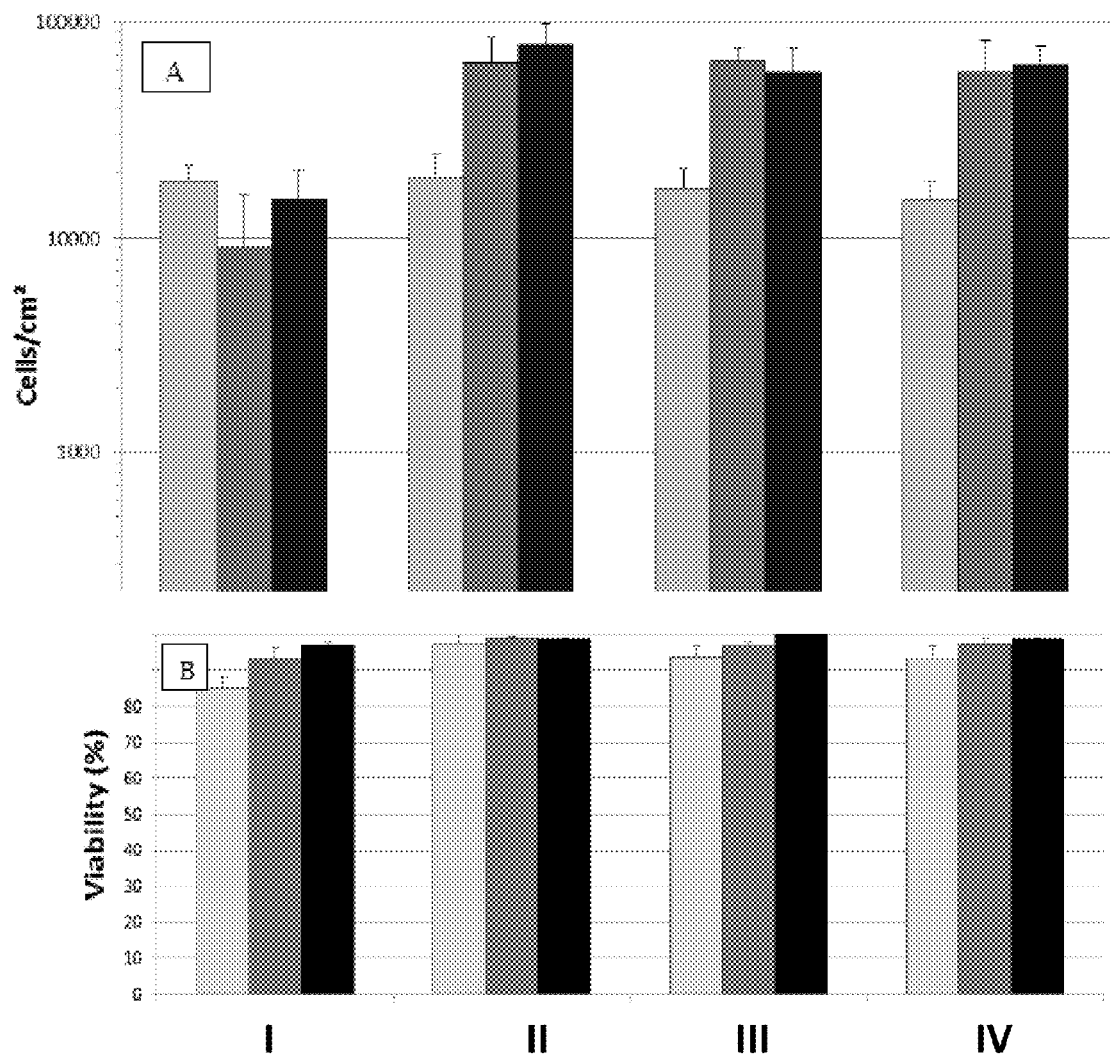
FIG. 5 shows (A) Cell density and (B) cell viability on the surface of various materials after 24 h ( ), 72 h ( ), 1 week , 2 weeks ( ) and 3 weeks ( ) of culture. Materials are: I: BSAm (10%) single network, II: PVAm (5%)-co BSAm(5%)/Fb, III: PVAm(3%)-co BSAm(7%)/Fb and IV: BSAm(10%)/Fb IPNs.
Figure 6:
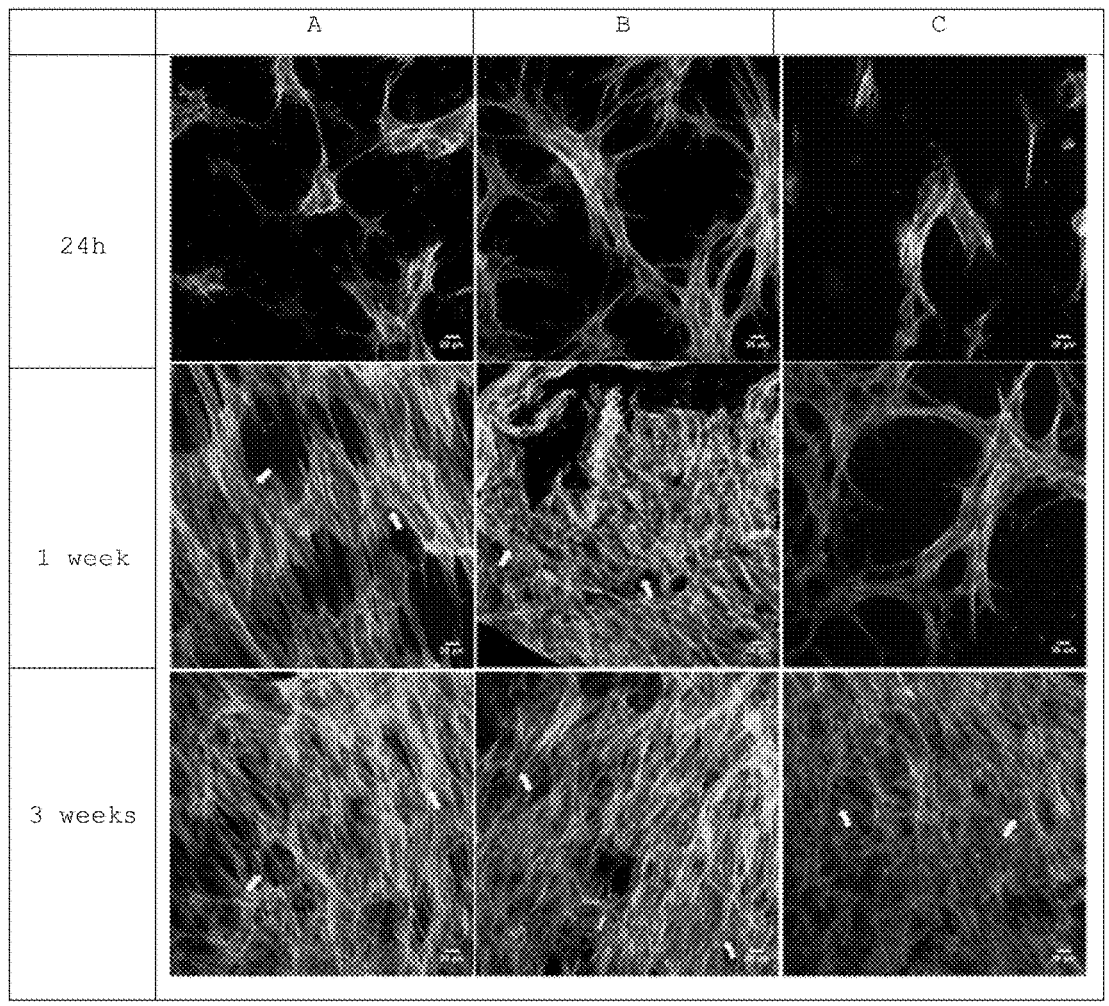
FIG. 6 shows cell secretion and remodeling of fibronectin with cytoskeleton and nucleus after 1 day (first row), 1 week (second row) and 3 weeks (third row) of culture on PVAm (5%)-co BSAm(5%)/Fb (first column A), PVAm(3%)-co BSAm(7%)/Fb (second column B) and BSAm(10%)/Fb (third column C) IPNs. Cells were observed with a x20 objective by CLSM (Zeiss LSM710). Scale bar: 20 μm.
Figure 7:
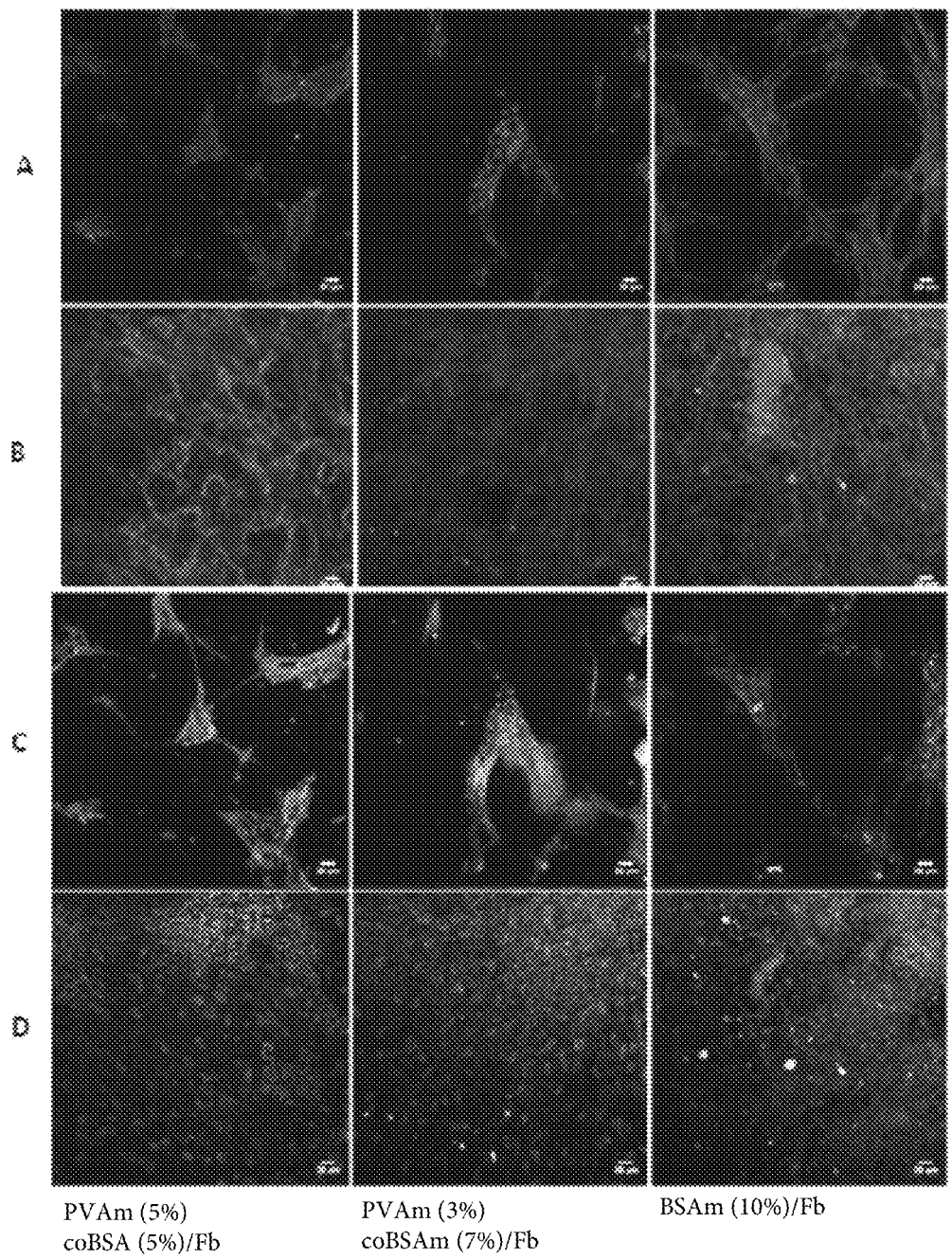
FIG. 7 shows cell secretion and remodeling of hyaluronic acid (A (first row), B (second row)) and type I collagen (C (third row), D (forth row)) with nucleus after 1 day (A (first row) and C (third row)) and 3 weeks (B (second row) and D (froth row)) of culture on PVAm(5%)coBSAm(5%)/Fb (first column), PVAm(3%)coBSAm(7%)/Fb (second column) and BSAm(10%)/Fb (third column) IPNs. Cells were observed with a x20 objective by CLSM (Zeiss LSM710). Scale bar: 20 μm.

Cell density was quantified to ascertain these observations. As shown in FIG. 5-A, this experiment reinforces the imaging observations. For comparison, previous experiments on non-biodegradable samples free of BSAm have shown that cells remained round shaped and their population decreased to 20% after one week on PVAm single network. Cells better adhered on PVAm(10%)/fibrin IPN, the cell population was maintained on the material surface for 1 week and spread, but no cell growth was observed. Here, on BSAm single network, cells seem to survive over 3 weeks but they do not proliferate while their number largely increases when cultivated on either BSAm(10%)/Fb IPN or PVAmcoBSAm/Fb IPNs. In polymer biomaterials, cell growth has been linked to biodegradability and the present results confirm this assumption.

The measure of cell viability (FIG. 5-B) comforts these observations. Cells rapidly die in contact to PVAm single network surface; the presence of fibrin in the PVAm(10%)/ Fb IPN slow down their death but this effect is not sufficient to allow their growth. When BSAm is present either into a single network or IPNs, the cell viability stays close to 100% after 3 weeks, indicating that the protein environment favors cell viability.

The IPNs synthesized with fibrin and BSAm have shown many interesting properties. Hence, on these biodegradable and fibrin based IPNs, cells truly survive and proliferate. However to consider a potential application in tissue engineering the maintaining of cell viability is not sufficient. Indeed, the cells on the materials must also be able to generate their own extracellular matrix and proceed to its remodeling to well settle on the material. The appearance of fibronectin, the first protein, and that of hyaluronic acid, the first polysaccharide neo-synthesized after fibrin gel formation in wound healing process (inflammatory phase) have been imaged by confocal laser scanning microscopy. The synthesis of fibronectin is important as this protein usually cross-link with fibrin to form the basis matrix for healing. Moreover, in healing, type III collagen is synthesized by fibroblasts during the proliferative phase and then later replaced by type I collagen during the remodeling phase allowing the further epithelialization. This step is a marker of ECM remodeling and maturation which indicates the good formation of ECM (composition and dynamics) by fibroblasts.

Fibronectin, hyaluronic acid and collagen I syntheses were followed on cell cultures also showing nuclei and the cytoskeleton as a function of time using 5 concomitant stainings. Fibronectin obviously appears upon time and this increase in concentration is similar for all materials for 24 h of culture. After a week, fibronectin is structured into fibers, which number increases after 3 weeks. Due to the low concentration of fibronectin in the culture medium, and the increasing amount of fibronectin visualized along the 3 weeks of cell culture it may be assumed that the observed fibronectin has been secreted by fibroblasts during their growth and development.

At 24 h, hyaluronic acid is detected at the surface and in the cytoplasm of the cells. After 3 weeks of culture, its presence has increased significantly. Comparing the stainings of fibronectin and hyaluronic acid, a large colocation is observable, which is consistent with the well-known affinity between these two macromolecules. Thus, in addition of fibronectin, fibroblasts secrete also hyaluronic acid during their growth on the biomaterials. This macromolecule is known to maintain good hydration of tissues.

From these analyses, it is shown that fibroblasts developing at the surface of these IPNs are able to neo-synthesize and secrete the first macromolecules that are usually produced by this cell line after their adhesion on an adapted support.

Monitoring of type I collagen is also particularly interesting. Indeed, this protein is the main component of the extracellular matrix of the dermis and its synthesis and deposition are essential for the formation of healthy tissue. However, in the healing process, fibroblasts first produce type III collagen at the early stages of healing (from 10 h to 3 days) while type I collagen replaces type III collagen only during the maturation phase. The appearance of collagen I thus come later in the healing process than that of fibronectin and hyaluronic acid and it is associated with a maturation of ECM. In order to verify its presence, collagen type I present on the surface of materials was immunostained. After 24 h of culture, type I collagen is already detected on the edges of the cells and then its presence increases significantly during the 3 weeks of culture. This staining intensification demonstrates that the cell population present on the material surface is capable of secreting it. It is known that induction of type I collagen synthesis requires a good cell spreading; the observation of type I collagen is an additional marker of the good state of fibroblasts on the surface of the IPNs.

This synthesis of fibronectin, hyaluronic acid and type I collagen was observed for all IPNs containing BSAm but was maximal for the PVAm(5%)coBSAm(5%)/Fb IPN.

The various IPNs formed with BSAm and fibrin or with different proportions of PVAm in addition to BSAm and fibrin are all capable of supporting cell growth on their surface. Fibroblasts cover the entirety of the material after 2 weeks of culture and show a high rate of survival; this allows qualifying these various materials as non-cytotoxic. Finally, cells grown on the surface of these biomaterials and secrete the key macromolecules of the human dermis ECM and are even able to structure them as fibers as it could be observed for fibronectin.

Conclusion

At this point, using BSAm alone or in addition to PVAm, various IPN materials including a fibrin gel were obtained. To our knowledge, the synthesis of a IPN constituted of a protein gel obtained through an enzymatic reaction and of the co-network of a functionalized synthetic polymer with a functionalized protein had never been described in the literature. Here several IPNs were obtained adding fibrin gel to a co-network made of various proportions of PVAm and BSAm. A one pot-one shot method was applied in each case leading to a rapid synthesis (from 2 to 15 minutes). The mechanical properties of all IPNs are good, they are all self-supported; the IPN architecture allowed improving the storage modulus of the fibrin gel by a factor ranging from 8 to 40 depending on the polymer composition. All materials are well synthesized and present an interpenetrated polymer networks architecture as shown by low soluble fraction. The protein networks (fibrin and BSAm) are homogeneously spread.

These biomaterials are biodegradable due to BSAm introduction inside the material. This new type of materials is the first co-network IPNs ever described in literature to be potentially biodegradable through fragmentation, then elimination. In addition, degradability helped to increase very significantly the bioactivity of materials.

A pertinent choice of the dyes and antibodies used has allowed us to perform concomitantly 5 different stainings on the same sample and to observe at the same time both the cell morphology and ECM remodeling. The utilization of such a large number of different fluorescent probes is totally original. When BSAm was used as a constituent of the Fb IPNs, the surface of the obtained materials can be completely covered by fibroblasts within two weeks, which was not the case of the PVAm/Fb IPN. In addition, cells at the surface of the material secrete the extracellular matrix biomacromolecules (fibronectin, hyaluronic acid) playing a key role in the early stages of wound healing and are able to structure them into fibers (fibronectin). The affinity properties of the molecules are identical to those of dermal fibroblasts (co-localization of fibronectin and hyaluronic acid). The good spreading of fibroblast cells on the surface of the materials allows them to produce type I collagen which is a protein characteristic of late maturation phase.

Encapsulation of Fibroblasts

To encapsulate fibroblasts in a PVAm (5%) coBSAm (5%)/Fb, IPN the precursors of fibrin gel (fibrinogen and thrombin) and those of the synthetic network (PVAm, BSAm and Irgacure 2959) were mixed in Tris buffer as detailed previously, and then the solution was then added to a concentrated fibroblast cells suspension. The resulting solution was placed in a mold and then exposed to UV for 1 hour at 37° C. for the synthesis of IPN. The material is then immersed in a culture medium to 37 h for 3 hours before repeating the medium to remove traces of synthesis buffer. The measurements were made on materials having 140 mm$^3$ and 1000000 cells each (ie 7000 cells/mm$^3$). Given the high cell concentration culture medium is changed every 3 days.

The material containing cells were frozen at −80° C. with and without 3% glycerol. After a rapid thawing at 37° C., the cells viability and cells proliferative activities were measured.

Results

Figure 8:
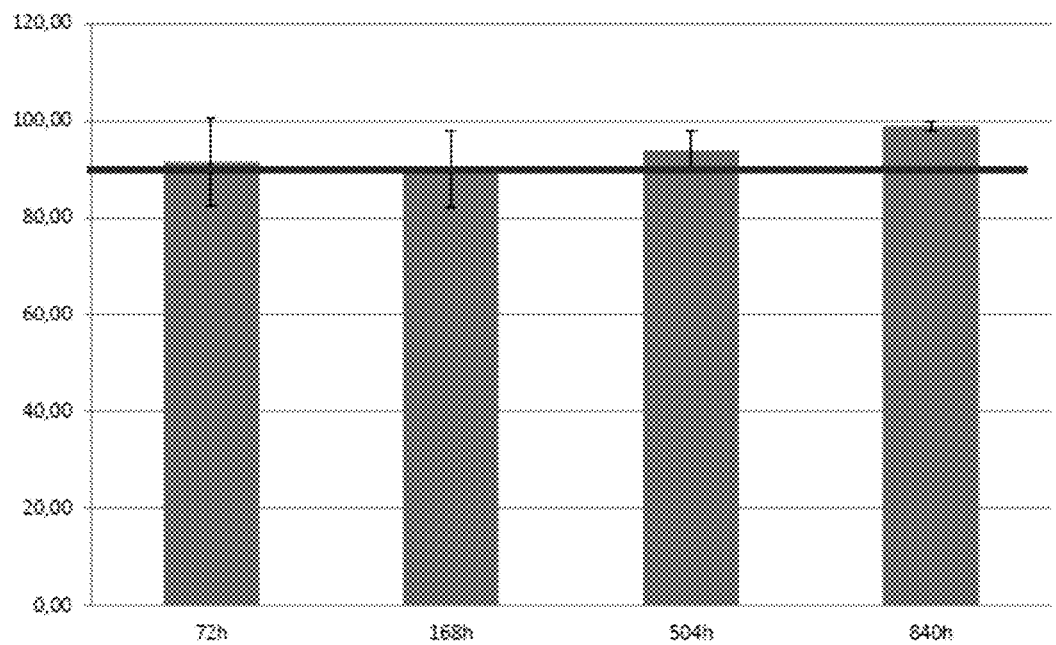
FIG. 8 shows the cell viability expressed as % of living cells according to Live/Dead test for different cultivation times (76 to 840 h) for fibroblast encapsulated in PVAm (5%)coBSAm(5%)/Fb IPN.

The cellular distribution and viability of the cells population are homogeneous in thickness throughout the material. The U.V exposure does not cause mortality of the cells on the surface of the material. After 1 and 3 weeks of culture, cell population is at least maintained and the distribution remains homogeneous. On FIG. 8 it can be seen that the cell viability remains identical during cultivation time from 72 h to 840 h. In addition, the cells initially present on the surface of the material are strongly expanded and cover the material. This distribution and the absence of mortality confirm that there is no impact of UV exposure on the cell population. About 3 weeks of culture, cell death is low and homogeneous within the material. The fact that the location of the cells in the depth of the material does not cause mortality suggests that the flow of nutrients and oxygen runs smoothly and there is no phenomenon of cellular hypoxia. After 3 weeks of culture, the average viability remains at or above 95%. These results confirm that cell encapsulation is possible in this matrix without toxicity.

From the point of view of cell morphology, after a short time of culture (24 hours) the cells are round regardless of the depth where they are located. After 1 week of culture, all the cells were elongated. Some cells show many very elongated pseudopodia. After 3 weeks, cells with numerous pseudopodia are preserved thoroughly. Similarly, the cells on the surface of the material are elongated and have a profile of fibroblasts.

It has been noticed that fibronectin is present after 24 hours of culture. Between 1 and 3 weeks of culture, a significant increase in the presence of fibronectin is visible within the depth of the material. In depth, fibronectin is located either around the cells or in the form of flakes. Similarly, the presence of collagen is detected as from 24 hours of culture in the IPN and increases significantly after one and three weeks of culture. Finally, it appears that its presence is greater within depth in the material than at its surface. These data confirm that fibroblasts retain their ability to secrete collagen when encapsulated in a matrix PVAm (5%) coBSAm (5%)/Fb IPN.

All of these results suggest that it is possible to produce cellularized dressings by encapsulation of fibroblasts within a material according to the invention such as PVAm (5%) coBSAm (5%)/Fb IPN. This type of material would be able to promote wound healing and secretion of extracellular matrix macromolecules such as fibronectin and collagen. The possibility of encapsulating living cells within the material of the invention and the capacity of the cells to proliferate in it makes this material capable of being used as a cellularized skin substitute for the treatment of burns for example.

Figure 9:
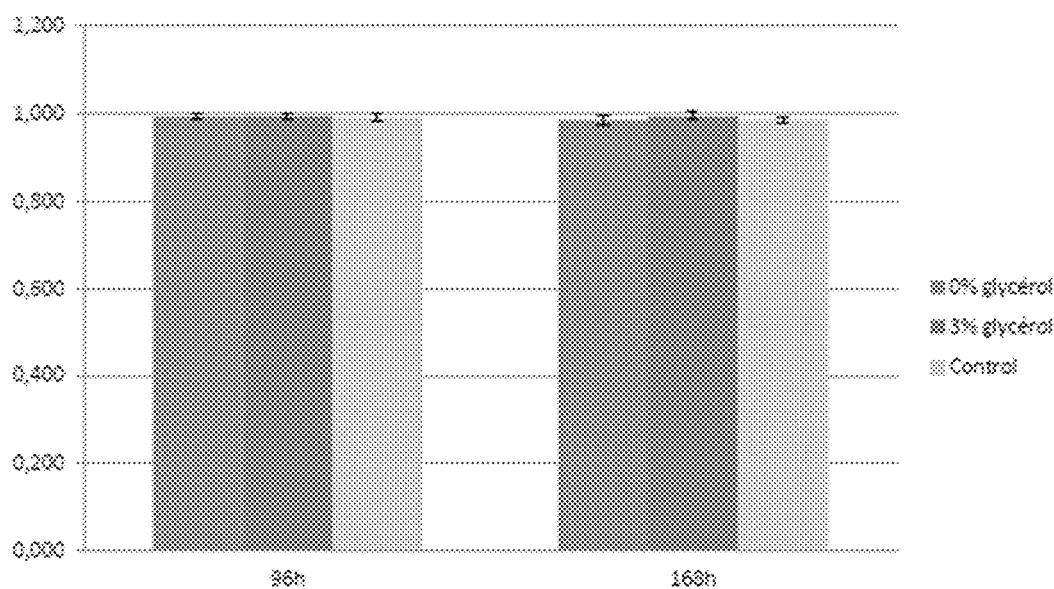
FIG. 9 shows the cell viability for different cultivation times (96 h and 168 h) after thawing for cryopreserved fibroblasts encapsulated in PVAm(5%)coBSAm(5%)/Fb IPN with 3% glycerol (dark grey) and without glycerol (middle grey) in comparison with the unfrozen control sample (light grey).
Figure 10:
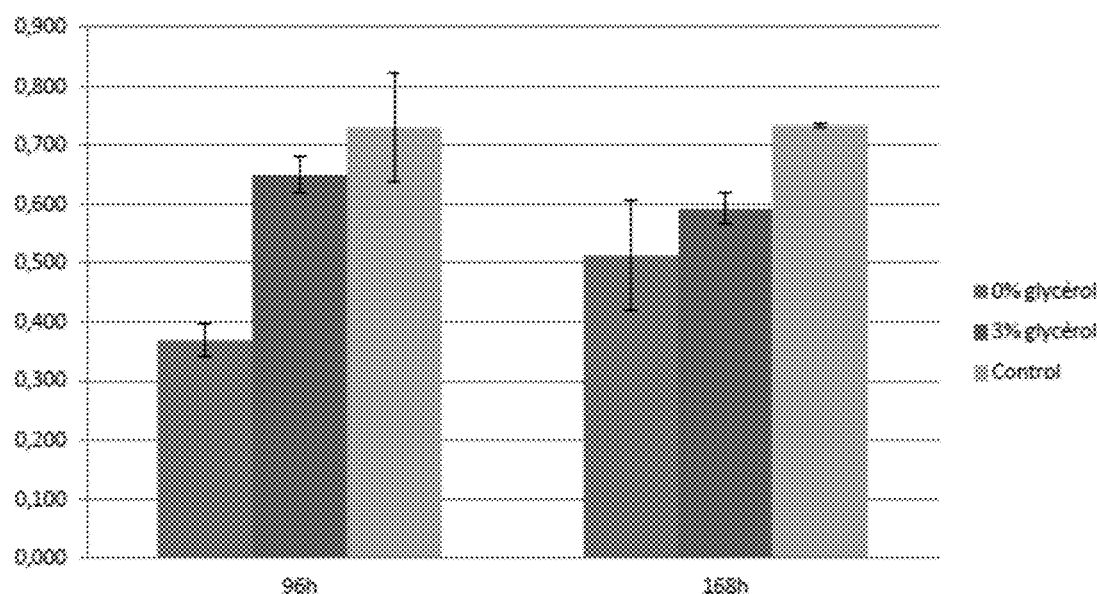
FIG. 10 shows the proliferative activity cells for different cultivation times (96 h and 168 h) after thawing for cryo-preserved fibroblasts encapsulated in PVAm(5%)coBSAm(5%)/Fb IPN with 3% glycerol (dark grey) and without glycerol (middle grey) in comparison with the unfrozen control sample (light grey).

As to frozen and unfrozen samples, the results shown in FIGS. 9 and 10 show that the viability of encapsulated cryopreserved fibroblasts remain at a level of 95% after 96 h and 168 h of cultivation after thawing (FIG. 9) with or without glycerol. This level is almost identical to the control level corresponding to non-frozen samples. As to the proliferative activity of the cryopreserved encapsulated cells, as seen from FIG. 10, the presence of 3% glycerol allows a quicker response in the restart of proliferative activity which is however not inhibited by the freezing.

The invention claimed is:

1. An interpenetrating polymer network (IPN) comprising a fibrin gel associated with a co-network of functionalized synthetic polymer cross-linked with a functionalized protein, wherein the protein is albumin functionalized with methacrylate groups and the synthetic polymer is polyvinyl alcohol (PVA) functionalized with methacrylate groups.

2. An interpenetrating polymer network (IPN) comprising a fibrin gel associated with a co-network of functionalized synthetic polymer cross-linked with a functionalized protein, obtained by a method comprising the steps of:
   i) preparing a first reaction mixture by introducing into a buffer:
      a. a fibrin gel forming precursor solution comprising fibrinogen or plasma,
      b. a synthetic polymer selected from the group consisting of polyvinyl alcohol (PVA), polyglycolic acid (PGA), polylactic acid (PLA), polycaprolactone (PCL), poly(N-vinylpyrrolidone), poly(2-hydroxy ethyl methacrylate) (PHEMA), polyethyleneoxide (PEO), and derivatives thereof, wherein the polymer is functionalized with grafted chemical groups X, X being selected in the group consisting of acrylate, methacrylate, vinyl, allyl and styrene and their derivatives,
      c. a serum albumin protein functionalized with grafted chemical groups X, wherein X has the same meaning as in b), and
      d. a polymerization initiator,
   ii) preparing a second reaction mixture by optionally adding a gelification activator of the formation of the fibrin gel to the first reaction mixture prepared in i),
   iii) incubating the reaction mixture obtained in i) or in ii) at a temperature and during a time sufficient to allow formation of the fibrin gel, and
   iv) performing a polymerizing and crosslinking of the functionalized synthetic polymer with the functionalized serum albumin protein.

3. The IPN according to claim 1 which is dehydrated and has a moisture content of about 2 to 10% in weight.

4. The IPN according to claim 1 characterized in that it further comprises living cells encapsulated therein.

5. The IPN according to claim 4, characterized in that it is frozen.

6. The IPN according to claim 1 for a wound dressing; surgical dressing; hemostatic dressing, for-delivering of therapeutic agents; coating of medical devices selected from the group consisting of stents, heart valves, catheters, vascular prosthetic filters; carrier for molecules selected from the group consisting of growth factors, antibiotics, bactericides, bacteriostats and enzymes or as support for eukaryotic cell culture with the material.

7. The IPN according to claim 1 for a skin substitute in the treatment of burns and skin repair or as a skin model with the material.

8. The IPN according to claim 3 having a moisture content of about 2 to 5% in weight.

9. The IPN according to claim 2 wherein the fibrin gel is a physical fibrin gel and the fibrin gel forming precursor solution is a fibrinogen solution.

10. The IPN according to claim 2 wherein the fibrin gel is a physical fibrin gel and the fibrin gel forming precursor solution is plasma.

11. The IPN according to claim 2 wherein the synthetic polymer is PVA and wherein the grafted functional group X is methacrylate.

12. The IPN according to claim 2 wherein the gelification activator of the formation of the fibrin gel is thrombin and/or calcium.

13. The IPN according to claim 2 wherein the step of incubating the reaction mixture obtained in i) or in ii) is achieved at a temperature comprised between 20° C. and 40° C.

14. The IPN according to claim 2 wherein the polymerization initiator is a photopolymerization initiator.

15. The IPN according to claim 2 wherein the functionalized synthetic polymer comprises at least two grafted chemical group X.

16. An interpenetrating polymer network (IPN) comprising a fibrin gel associated with a co-network of functionalized synthetic polymer cross-linked with a functionalized protein, obtained by a method comprising the steps of:
   i) preparing a first reaction mixture by introducing into a buffer:
      a. a fibrinogen solution,
      b. polyvinyl alcohol (PVA) functionalized with methacrylate groups,
      c. an albumin functionalized with methacrylate groups, and
      d. a polymerization initiator,
   ii) preparing a second reaction mixture by optionally adding a gelification activator for the formation of the fibrin gel to the first reaction mixture prepared in i),
   iii) incubating the reaction mixture obtained in i) or in ii) at a temperature and during a time sufficient to allow formation of the fibrin gel, iv) performing a polymerizing and crosslinking of the PVA functionalized with methacrylate groups with the albumin functionalized with methacrylate groups, and v.) drying the material to a moisture content comprised between 2 to 10% in weight.

17. The IPN according to claim 2 which is dehydrated and has a moisture content of about 2 to 10% in weight.

18. The IPN according to claim 2 characterized in that it further comprises living cells encapsulated therein.

19. The IPN according to claim 2 for a wound dressing; surgical dressing; hemostatic dressing, for-delivering of therapeutic agents; coating of medical devices selected from the group consisting of stents, heart valves, catheters, vascular prosthetic filters; carrier for molecules selected from the group consisting of growth factors, antibiotics, bactericides, bacteriostats and enzymes or as support for eukaryotic cell culture with the material.

* * * * *

UNITED STATES PATENT AND TRADEMARK OFFICE
CERTIFICATE OF CORRECTION

PATENT NO. : 9,512,279 B2  
APPLICATION NO. : 14/132410  
DATED : December 6, 2016  
INVENTOR(S) : Laurent Bidault et al.

Page 1 of 1

It is certified that error appears in the above-identified patent and that said Letters Patent is hereby corrected as shown below:

On the Title Page

Under Assignee, Item (73):
Please delete "Universite Cegy-Pontoise, Cergy (FR)" and insert -- Universite Cergy-Pontoise, Cergy (FR) --

Signed and Sealed this  
Eleventh Day of July, 2017

Joseph Matal  
*Performing the Functions and Duties of the*  
*Under Secretary of Commerce for Intellectual Property and*  
*Director of the United States Patent and Trademark Office*